(12) United States Patent
Laudo

(10) Patent No.: US 7,978,405 B2
(45) Date of Patent: *Jul. 12, 2011

(54) OPTICAL SYSTEM FOR CELL IMAGING

(75) Inventor: John S. Laudo, Hilliard, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/168,373

(22) Filed: Jul. 7, 2008

(65) Prior Publication Data

US 2008/0266658 A1    Oct. 30, 2008

Related U.S. Application Data

(63) Continuation of application No. 11/261,105, filed on Oct. 27, 2005, now Pat. No. 7,397,601.

(60) Provisional application No. 60/631,025, filed on Nov. 24, 2004, provisional application No. 60/631,026, filed on Nov. 24, 2004, provisional application No. 60/631,027, filed on Nov. 24, 2004.

(51) Int. Cl.
*G02B 21/06* (2006.01)
*G02B 13/20* (2006.01)

(52) U.S. Cl. .................. 359/385; 359/368; 359/599

(58) Field of Classification Search .......... 359/368–398, 359/619, 634, 599
See application file for complete search history.

(56) References Cited

U.S. PATENT DOCUMENTS

| | | |
|---|---|---|
| 2,635,194 A | 4/1953 | Kellogg et al. |
| 2,677,304 A | 5/1954 | Wallingford |
| 2,902,151 A | 9/1959 | Miles et al. |
| 3,027,798 A | 4/1962 | Mathias |
| 3,030,516 A | 4/1962 | Seavey |
| 3,160,760 A | 12/1964 | Fry et al. |
| 3,245,529 A | 4/1966 | Doud |
| 3,262,561 A | 7/1966 | Sorbie |
| 3,529,169 A | 9/1970 | Heaney et al. |
| 3,627,276 A | 12/1971 | Gilford |
| 3,814,248 A | 6/1974 | Lawhead |

(Continued)

FOREIGN PATENT DOCUMENTS

EP          0919812 A2     11/1998

(Continued)

OTHER PUBLICATIONS

Ts'o et al., "'Blood Biopsy' for Epithelial Cancer Cells Based on Circulating Cancer Cell Tests," Cell works Inc., 2001 (abstract from 2$^{nd}$ Principal Investigators Meeting, IMAT, last accessed Jul. 7, 2008).

(Continued)

*Primary Examiner* — Thong Nguyen

(74) *Attorney, Agent, or Firm* — Fay Sharpe LLP

(57) ABSTRACT

A microscope system (10, 10', 10", 10''') includes a laser (18) or light emitting diode (18''') that generates source light having a non-uniform spatial distribution. An optical system includes an objective (40) defining a field of view, and an optical train (22, 22', 22", 22''') configured to convert the source light into an enlarged-diameter collimated light, to spatially homogenize the enlarged-diameter collimated light, and to couple the homogenized enlarged-diameter collimated light into the objective to provide substantially uniform static illumination of the field of view. A camera system (56) is statically optically coupled by the objective with at least most of the field of view.

15 Claims, 15 Drawing Sheets

U.S. PATENT DOCUMENTS

| | | | | |
|---|---|---|---|---|
| 4,156,570 | A | 5/1979 | Wardlaw | |
| 4,717,660 | A | 1/1988 | Schulte | |
| 4,744,615 | A | 5/1988 | Fan et al. | |
| 4,952,054 | A | 8/1990 | Levine et al. | |
| 5,067,805 | A | 11/1991 | Corle et al. | |
| 5,086,784 | A | 2/1992 | Levine et al. | |
| 5,101,295 | A | 3/1992 | Lichtman et al. | |
| 5,166,813 | A | 11/1992 | Metz | |
| 5,224,200 | A | 6/1993 | Rasmussen et al. | |
| 5,251,474 | A | 10/1993 | Wardlaw et al. | |
| 5,252,460 | A | 10/1993 | Fiedler et al. | |
| 5,282,981 | A | 2/1994 | Adams et al. | |
| 5,308,506 | A | 5/1994 | McEwen et al. | |
| 5,331,468 | A | 7/1994 | Noethen | |
| 5,377,004 | A | 12/1994 | Owen et al. | |
| 5,393,674 | A | 2/1995 | Levine et al. | |
| 5,403,714 | A | 4/1995 | Levine et al. | |
| 5,496,704 | A | 3/1996 | Fiedler et al. | |
| 5,534,386 | A | 7/1996 | Petersen et al. | |
| 5,548,661 | A | 8/1996 | Price et al. | |
| 5,556,764 | A | 9/1996 | Sizto et al. | |
| 5,606,129 | A | 2/1997 | Lehmann | |
| 5,609,939 | A | 3/1997 | Petersen et al. | |
| 5,610,733 | A | 3/1997 | Feldman et al. | |
| 5,677,762 | A | 10/1997 | Ortyn et al. | |
| 5,754,693 | A | 5/1998 | Takesue et al. | |
| 5,757,954 | A | 5/1998 | Kuan et al. | |
| 5,790,692 | A | 8/1998 | Price et al. | |
| 5,790,710 | A | 8/1998 | Price et al. | |
| 5,835,266 | A | * 11/1998 | Kitajima | 359/384 |
| 5,875,258 | A | 2/1999 | Ortyn et al. | |
| 5,889,584 | A | 3/1999 | Wardlaw | |
| 5,933,519 | A | 8/1999 | Lee et al. | |
| 5,943,129 | A | 8/1999 | Hoyt et al. | |
| 5,956,106 | A | 9/1999 | Petersen et al. | |
| 5,987,158 | A | 11/1999 | Meyer et al. | |
| 5,999,844 | A | 12/1999 | Gombrich et al. | |
| 6,002,474 | A | 12/1999 | Thomas et al. | |
| 6,025,938 | A | 2/2000 | Kathman et al. | |
| 6,049,421 | A | * 4/2000 | Raz et al. | 359/394 |
| 6,072,631 | A | 6/2000 | Guenther et al. | |
| 6,081,326 | A | 6/2000 | Rousseau et al. | |
| 6,081,381 | A | * 6/2000 | Shalapenok et al. | 359/619 |
| 6,081,740 | A | 6/2000 | Gombrich et al. | |
| 6,094,274 | A | 7/2000 | Yokoi | |
| 6,137,899 | A | 10/2000 | Lee et al. | |
| 6,141,096 | A | 10/2000 | Stern et al. | |
| 6,153,148 | A | 11/2000 | Thomas | |
| 6,154,282 | A | 11/2000 | Lilge et al. | |
| 6,157,756 | A | 12/2000 | Ishiwata | |
| 6,169,289 | B1 | 1/2001 | White et al. | |
| 6,175,420 | B1 | 1/2001 | Barry et al. | |
| 6,185,030 | B1 | 2/2001 | Overbeck | |
| 6,197,523 | B1 | 3/2001 | Rimm et al. | |
| 6,215,892 | B1 | 4/2001 | Douglass et al. | |
| 6,221,596 | B1 | 4/2001 | Yemini et al. | |
| 6,236,459 | B1 | * 5/2001 | Negahdaripour et al. | 356/496 |
| 6,236,881 | B1 | 5/2001 | Zahler et al. | |
| 6,239,871 | B1 | 5/2001 | Gilby | |
| 6,246,524 | B1 | 6/2001 | Tanaka | |
| 6,252,236 | B1 | 6/2001 | Trulson et al. | |
| 6,259,807 | B1 | 7/2001 | Ravkin | |
| 6,284,142 | B1 | 9/2001 | Muller | |
| 6,285,450 | B1 | 9/2001 | Thomas et al. | |
| 6,294,094 | B1 | 9/2001 | Muller et al. | |
| 6,295,168 | B1 | 9/2001 | Hoffnagle et al. | |
| 6,330,058 | B1 | 12/2001 | Garcia-Rubio et al. | |
| 6,330,349 | B1 | 12/2001 | Hays et al. | |
| 6,344,653 | B1 | 2/2002 | Webb et al. | |
| 6,352,502 | B1 | 3/2002 | Chaiken et al. | |
| 6,365,104 | B1 | 4/2002 | Brinster et al. | |
| 6,388,746 | B1 | 5/2002 | Eriksson et al. | |
| 6,419,822 | B2 | 7/2002 | Muller et al. | |
| 6,429,411 | B1 | 8/2002 | Iwasaki et al. | |
| 6,429,897 | B2 | 8/2002 | Derndinger et al. | |
| 6,444,436 | B1 | 9/2002 | Rimm et al. | |
| 6,455,861 | B1 | 9/2002 | Hoyt | |
| 6,459,484 | B1 | 10/2002 | Yokoi | |
| 6,670,197 | B2 | 12/2003 | Rimm et al. | |
| 6,672,739 | B1 | 1/2004 | Argyle et al. | |
| 7,001,055 | B1 | * 2/2006 | Lange | 362/551 |
| 7,397,601 | B2 | * 7/2008 | Laudo | 359/385 |
| 2001/0024802 | A1 | 9/2001 | Rimm et al. | |
| 2002/0001090 | A1 | 1/2002 | Cemic et al. | |
| 2002/0014462 | A1 | 2/2002 | Muller | |
| 2002/0061542 | A1 | 5/2002 | Rimm et al. | |
| 2002/0164810 | A1 | 11/2002 | Dukor et al. | |
| 2003/0096324 | A1 | 5/2003 | Matveev et al. | |
| 2003/0142399 | A1 | 7/2003 | Schoeppe | |
| 2003/0205538 | A1 | 11/2003 | Dorian et al. | |
| 2004/0067536 | A1 | 4/2004 | Haubert et al. | |
| 2005/0018195 | A1 | * 1/2005 | Lex | 356/445 |

FOREIGN PATENT DOCUMENTS

| | | | |
|---|---|---|---|
| WO | WO 03/097088 A2 | 5/2003 | |
| WO | WO 2004/000420 A1 | 6/2003 | |
| WO | WO 2004/090604 A2 | 3/2004 | |
| WO | WO 2005/045396 A2 | 11/2004 | |

OTHER PUBLICATIONS

Dunn et al., "Introduction to Confocal Microscopy," Nikon MicroscopyU, at http://www.microscopyu.com/articles/confocal/, Small World Gallery, 3 pages, 2000-2005.

Ashley et al., "Holographic data storage," IBM Journal of Research and Development. vol. 44, No. 3, pp. 341-366, 2000.

Physical Optics Corporation, at http://www.poc.com/lsd/, pp. 8, 2003.

Wadle et al., "Holographic Diffusers: Diffusers with low backscatter," J. Modern Optics, 42, 1387-1396, 1995.

* cited by examiner

US 7,978,405 B2

OPTICAL SYSTEM FOR CELL IMAGING

This is a continuation application of application Ser. No. 11/261,105, filed Oct. 27, 2005 (which has since issued as U.S. Pat. No. 7,397,601), which claims the benefit of U.S. Provisional Application No. 60/631,025, filed Nov. 24, 2004, U.S. Provisional Application No. 60/631,026, filed Nov. 24, 2004, and U.S. Provisional Application No. 60/631,027, filed Nov. 24, 2004, which is incorporated by reference herein in its entirety. Application Ser. No. 11/261,105, filed Oct. 27, 2005 is incorporated by reference herein in its entirety. Provisional Application No. 60/631,025, filed Nov. 24, 2004 is incorporated by reference herein in its entirety. Provisional Application No. 60/631,026, filed Nov. 24, 2004 is incorporated by reference herein in its entirety. Provisional Application No. 60/631,027, filed Nov. 24, 2004 is incorporated by reference herein in its entirety.

BACKGROUND

The following relates to the imaging arts. It is described with particular reference to example embodiments that relate to imaging of rare cells, such as epithelial cells, in the buffy coat of a centrifuged blood sample. However, the following relates more generally to illumination systems for generating a substantially uniform static illumination across a large field of view and to microscopes employing same.

In the technique of quantitative buffy coat analysis, a whole blood sample is drawn and processed using anti-coagulant additives, centrifuging, and so forth to separate the blood into components including a huffy coat component comprised principally of white blood cells. Rare cells of interest which are present in the buffy coat, such as certain epithelial cells associated with certain cancers, are tagged using a suitable fluorescent dye, and fluorescence microscopic imaging is then used to count the fluorescent dye-tagged cells of interest. Quantitative buffy coat analysis is a promising non-invasive technique for screening for certain cancers, for monitoring cancer treatment, and so forth.

The concentration of fluorescent dye-tagged rare cells in the buffy coat is low. Optical scanning fluorescence microscopy enables assessment of a large area of buffy coat sample by scanning a field of view of a microscope relative to the buffy coat sample. Scanning can be achieved by moving the microscope relative to the buffy coat sample, by moving the buffy coat sample relative to the microscope, or by some combination thereof. A large field of view illuminated with high intensity uniform light is advantageous for rapidly and accurately assaying the fluorescent dye-tagged rare cells in the buffy coat sample. The illumination may also advantageously employ monochromatic or narrow-bandwidth light so as to facilitate spectral differentiation between rare cell fluorescence and scattered illumination.

However, providing illumination at high intensity that is uniform over a large field of view is difficult.

In the case of white light sources, filtering is typically required to provide monochromatic or at least spectrally restricted illumination. Spectral filtering blocks a large portion of the optical output that lies outside the selected spectral range. Thus, illuminating with a white light source is optically inefficient. High intensity incandescent white light sources such as Xenon lamps also produce substantial heat, which can adversely affect the quantitative buffy coat analysis.

A laser light source is more optically efficient at producing spectrally narrow light. For example, an argon laser outputs high intensity narrow spectral lines at 488 nm and 514 nm, and weaker lines at other wavelengths. These wavelengths are suitable for exciting luminescence in certain tagging dyes that luminesce at about 550 nm.

However, lasers typically output a tightly collimated beam having a highly non-uniform Gaussian intensity profile or distribution across a narrow beam cross-sectional area. Moreover, the laser beam is coherent and typically exhibits a speckle pattern due to interference amongst the wave fronts. The speckle pattern can have spatial frequencies that overlap the typical size of rare cells. The speckle pattern can also shift or change as the field of view is scanned. These aspects of laser light substantially complicate determination of whether a detected luminous feature is a fluorescent dye-tagged rare cell, or an illumination artifact.

Spatial uniformity can be improved using a beam homogenizer. One type of beam homogenizer operates by providing an inverse Gaussian absorption profile that substantially cancels the Gaussian beam distribution. Another type of beam homogenizer employs two or more lenses (or a compound lens) to refract the Gaussian beam in a way that redistributes the light into a flattened spatial profile. Using a beam homogenizer in microscopic fluorescence imaging is problematic, however, because focusing of the homogenized beam by the microscope objective can introduce additional beam non-uniformities. Moreover, beam homogenizers generally do not substantially reduce speckle non-uniformities.

In another approach, known as confocal microscopy, the laser beam is rapidly rastered or scanned across the field of view. The field of view is sampled rather than imaged as a whole. In this dynamic approach, the portion of the sample illuminated at any given instant in time is much smaller than the field of view. By rapidly mastering the focused laser beam over the field of view, an image can be constructed from the acquired sample points. A uniform illumination is, in effect, dynamically simulated through rapid sampling of the field of view.

Confocal microscopy is an established technique. However, the beam mastering adds substantial complexity and cost to the microscope system. Confocal microscopy can also be highly sensitive to small defects in a lenses or other optical component. Thus, very high quality optics should be employed, which again increases system cost.

INCORPORATION BY REFERENCE

U.S. application Ser. No. 10/263,974 filed Oct. 3, 2002 and published as U.S. Publ. Appl. No. 2004/0067162 A1 on Apr. 8, 2004, is incorporated by reference herein in its entirety.

U.S. application Ser. No. 10/263,975 filed Oct. 3, 2002 and published as U.S. Publ. Appl. No. 2004/0067536 A1 on Apr. 8, 2004, is incorporated by reference herein in its entirety.

U.S. patent application Ser. No. 11/261,306 filed Oct. 27, 2005, entitled "Method and Apparatus for Detection of Rare Cells", inventor Albert E. Weller, III, and is incorporated by reference herein in its entirety.

U.S. patent application Ser. No. 11/261,104 filed Oct. 27, 2005, entitled "Sample Tube Handling Apparatus", inventors Steve Grimes, Thomas D. Haubert, and Eric R. Navin, and is incorporated by reference herein in its entirety.

BRIEF SUMMARY

According to one aspect, an optical system is disclosed for imaging a microscope field of view. An is objective is focused on the microscope field of view. An optical train includes one or more stationary optical components configured to receive source light having a non-uniform spatial distribution and to output a corrected spatial distribution to the objective that when focused by the objective at the microscope field of view provides substantially uniform static illumination over substantially the entire microscope field of view.

According to another aspect, a microscope system is disclosed. A laser, semiconductor laser diode, or light emitting diode generates source light having a non-uniform spatial distribution. An optical system includes (i) an objective defining a field of view and (ii) an optical train configured to convert the source light into an enlarged-diameter collimated light, spatially homogenize the enlarged-diameter collimated light, and couple the homogenized enlarged-diameter collimated light into the objective to provide substantially uniform static illumination of the field of view. A camera system is statically optically coupled by the objective with at least most of the field of view.

According to another aspect, an optical system is disclosed for imaging a microscope field of view. An objective is focused on the microscope field of view. A stationary diffuser receives source light having a non-uniform spatial distribution and diffuses the source light to improve spatial uniformity. The diffused light is used to provides substantially uniform static illumination over at least most of the microscope field of view through the objective.

Numerous advantages and benefits of the present invention will become apparent to those of ordinary skill in the art upon reading the following detailed description of the preferred embodiments.

BRIEF DESCRIPTION OF THE DRAWINGS

The invention may take form in various components and arrangements of components, and in various process operations and arrangements of process operations. The drawings are only for the purpose of illustrating preferred embodiments and are not to be construed as limiting the invention.

FIG. 5 shows a perspective view of the holder, with the housing shown in phantom to reveal internal components.

FIG. 6 shows a side view of the holder, with the housing shown in phantom.

FIG. 7 shows a perspective view of the test tube and alignment and biasing bearings.

FIG. 8 shows a top view of the test tube holder including an indication of bias force.

FIG. 9 shows a side view of a second end of the test tube including a contoured base.

FIG. 10 shows a top view of the rotational coupler including a contour configured to mate with the contoured base of the test tube shown in FIG. 9.

DETAILED DESCRIPTION OF THE PREFERRED EMBODIMENTS

Figure 1:
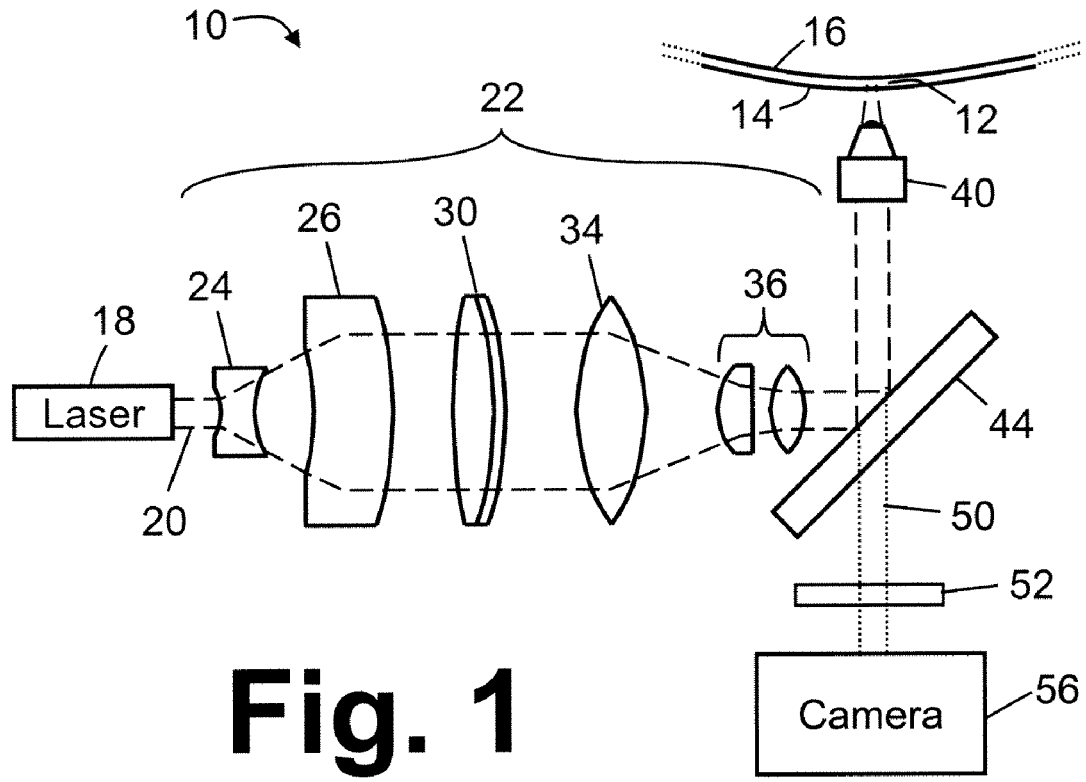
FIG. 1 diagrammatically shows a microscope system including an optical system for providing substantially uniform static illumination over substantially the entire microscope field of view.

With reference to FIG. 1, a microscope system 10 images a microscope field of view coinciding with a buffy coat sample disposed in a generally planar portion of an annular gap 12 between a light-transmissive test tube wall 14 and a float wall 16 of a float disposed in the test tube. Suitable methods and apparatuses for acquiring and preparing such buffy coat samples are disclosed, for example, in U.S. Publ. Appl. No. 2004/0067162 A1 and U.S. Publ. Appl. No. 2004/0067536 A1.

The microscope field of view is generally planar in spite of the curvatures of the test tube and the float, because the microscope field of view is typically much smaller in size than the radii of curvature of the test tube wall 14 and the float wall 16. Although the field of view is substantially planar, the buffy coat sample disposed between the light-transmissive test tube wall 14 and the float wall 16 may have a thickness that is substantially greater than the depth of view of the microscope system 10.

The test tube is mounted in fixed position respective is to the microscope system 10 in a manner conducive to scanning the microscope field of view across the annular gap. As will be discussed, suitable mechanisms are preferably provided for effectuating relative rotational and/or translational scanning of the field of view over the annular gap containing the buffy coat sample.

The microscope system 10 includes a laser 18, such as a gas laser, a solid state laser, a semiconductor laser diode, or so forth, that generates source light 20 (diagrammatically indicated in FIG. 1 by dashed lines) in the form of a laser beam having an illumination wavelength and a non-uniform spatial distribution that is typically Gaussian or approximately Gaussian in shape with a highest intensity in a central region of the beam and reduced intensity with increasing distance from the beam center. An optical train 22 is configured to receive the spatially non-uniform source light 20 and to output a corrected spatial distribution.

A beam spreader includes a concave lens 24 that generally diverges the laser beam, and a collimating lens 26 that collimates the spread beam at a larger diameter that substantially matches the diameter of a Gaussian spatial characteristic of a beam homogenizer 30. The beam homogenizer 30 flattens the expanded laser beam by substantially homogenizing the Gaussian or other non-uniform distribution of the source light to produce output light having improved spatial uniformity.

In some embodiments, the beam homogenizer 30 operates by having a spatially non-uniform absorption profile that corresponds to an inverse-Gaussian. In such embodiments, the beam homogenizer has highest absorption in a central region corresponding to the highest intensity central region of the expanded laser beam, and has a lower absorption, or no absorption, in the periphery corresponding to the lower intensity outer regions of the expanded laser beam.

In other embodiments, the beam homogenizer 30 refractively redistributes the light to homogenize the light intensity across the area of the expanded laser beam, for example using a suitable lens pair. Refractive beam homogenizers refract light from the high intensity central region of the expanded laser beam into the lower intensity periphery regions.

A focusing lens 34 and cooperating lenses 36 reduce the expanded and flattened or homogenized laser beam down to a desired beam diameter for input to an objective 40 that is focused on the microscope field of view. A dichroic mirror 44 is selected to substantially reflect light at the wavelength or wavelength range of the laser beam, and to substantially transmit light at the fluorescence wavelength or wavelength range of the fluorescent dye used to tag rare cells in the buffy coat sample.

The optical train 22 including the stationary optical components 24, 26, 30, 34, 36 is configured to output a corrected spatial distribution to the objective 40 that when focused by the objective 40 at the microscope field of view provides substantially uniform static illumination over substantially the entire microscope field of view. The objective 40 focuses the corrected illumination onto the microscope field of view. The objective 40 may include a single objective lens, or may include two or more objective lenses. The focus depth of the microscope system is adjustable, for example by adjusting a distance between the objective 40 and the light-transmissive test tube wall 14. Additionally or alternatively, the focus depth may be adjusted by relatively moving two or more lenses or lensing elements within the objective 40.

The beam homogenizer 30 is designed to output a substantially uniform homogenized beam for a Gaussian input beam of the correct diameter. However, the objective 40 typically introduces some spatial non-uniformity. Accordingly, one or more of the stationary optical components, such as the spreading lens 24, collimating lens 26, focusing lens 34, and/or focusing lenses 36 are optionally configured to introduce spatial non-uniformity into the spatial distribution such that the beam when focused by the objective 40 provides substantially uniform static illumination of the microscope field of view. In some contemplated embodiments, this corrective spatial non-uniformity is introduced by one or more dedicated optical components (not shown) that are included in the optical train 22 for that purpose.

The substantially uniform static illumination of the microscope field of view causes fluorescence of any fluorescent dye-tagged epithelial cells disposed within the microscope field of view. Additionally, the fluorescent dye typically imparts a lower-intensity background fluorescence to the buffy coat. The fluorescence is captured by the objective 40, and the captured fluorescence 50 (diagrammatically indicated in FIG. 1 by dotted lines) passes through the dichroic mirror 44, and through an optional filter 52 for removing any stray source light, to be imaged by a camera system 56. The camera system 56 may, for example, include a charge coupled device (CCD) camera for acquiring electronic images that can be stored in a computer, memory card, or other non-volatile memory for subsequent image processing.

Figure 2:
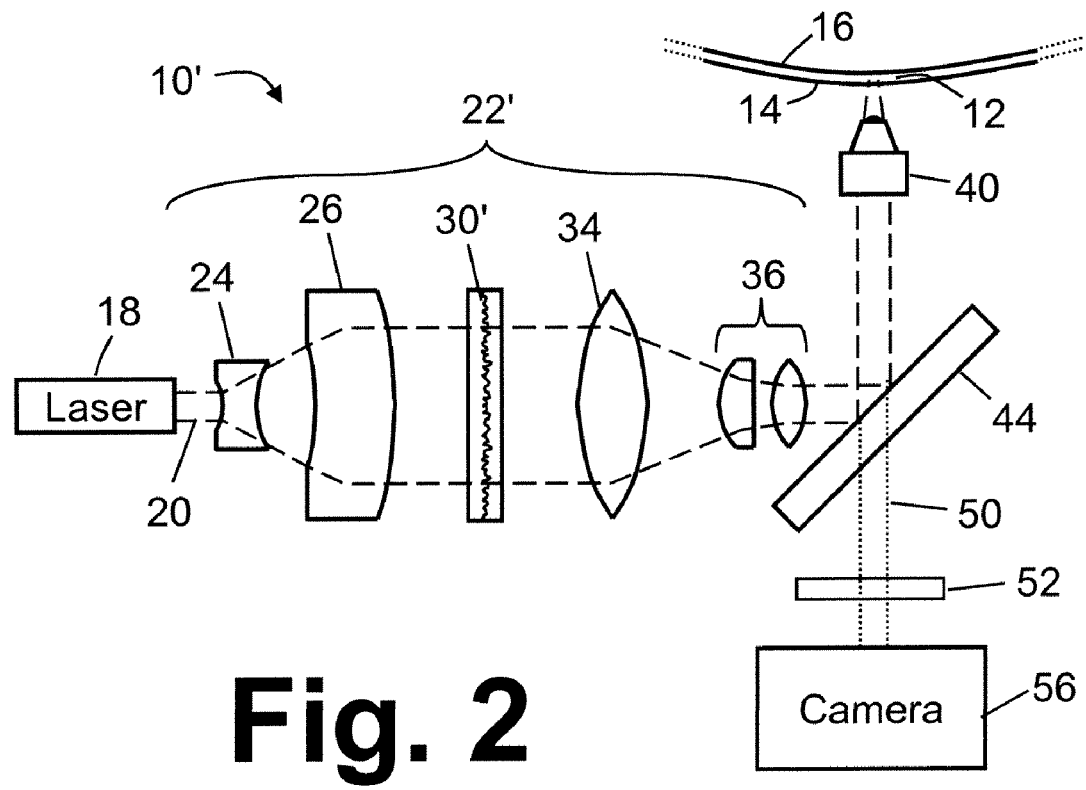
FIG. 2 diagrammatically shows the microscope system of FIG. 1 with a modified optical system.
Figure 3:
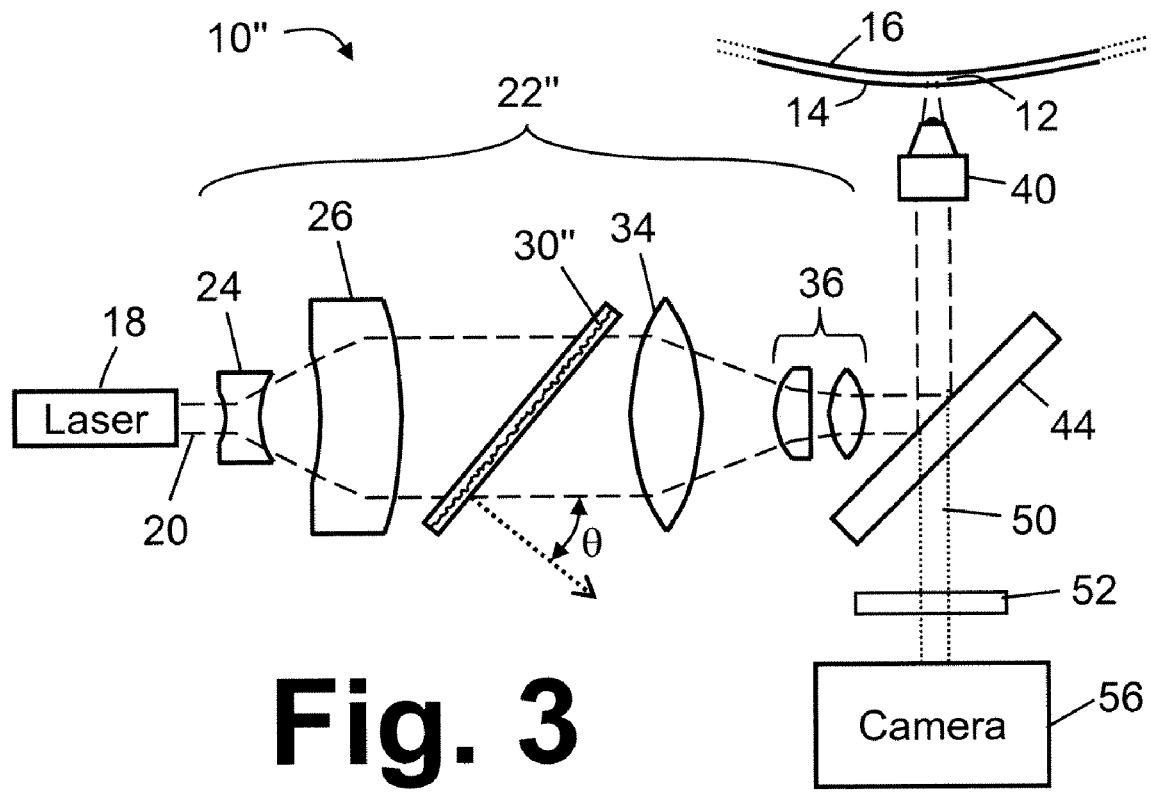
FIG. 3 diagrammatically shows the microscope system of FIG. 1 with another modified optical system.

With reference to FIGS. 2 and 3, other suitable microscope systems are described.

FIG. 2 shows a microscope system 10' that is similar to the microscope system 10 of FIG. 1, except that the optical train 22' differs in that the stationary beam homogenizer 30 of FIG. 1 is replaced by a stationary diffuser 30'. The diffuser 30' may, for example, be a holographic diffuser available, for example, from Physical Optics Corporation (Torrance, Calif.). Such holographic diffusers employ a hologram providing randomizing non-periodic optical structures that diffuse the light to impart improved spatial uniformity. However, the diffusion of the light also imparts some concomitant beam divergence. Typically, stronger diffusion of the light tend to impart more spatial uniformity, but also tends to produce greater beam divergence. Holographic diffusers are suitably classified according to the full-width-at-half-maximum (FWHM) of the divergence angle, with larger divergence angles typically providing more diffusion and greater light uniformity, but also leading to increased light loss in the microscope system 10' due to increased beam divergence.

In some embodiments of the microscope system 10', the diffuser 30' is a low-angle diffuser having a FWHM less than or about 10°. Lower angle diffusers are generally preferred to provide less divergence and hence better illumination throughput efficiency; however, if the divergence FWHM is too low, the diffuser will not provide enough light diffusion to impart adequate beam uniformity. Low diffusion reduces the ability of the diffuser 30' to homogenize the Gaussian distribution, and also reduces the ability of the diffuser 30' to remove speckle.

With reference to FIG. 3, another embodiment microscope system 10" is similar to the microscope system 10', and includes an optical train 22" that employs a diffuser 30" similar to the diffuser 30' of the microscope system 10'. However, the diffuser 30" is tilted at an angle $\theta$ respective to the optical path of the optical train 22" so as to substantially reduce a speckle pattern of the source light 20. Without being limited to any particular theory of operation, it is believed that the tilting shifts the speckle pattern to higher spatial frequencies, in effect making the speckle size smaller. The speckle size is spatially shifted by the tilting such that the frequency-shifted speckle is substantially smaller than an imaging pixel size.

In some embodiments, a tilt angle $\theta$ of at least about 30° respective to the optical path of the optical train 22" is employed, which has been found to substantially reduce speckle for diffusers 30" having a FWHM as low as about 5°. On the other hand, tilt angles $\theta$ of greater than about 45° have been found to reduce illumination throughput efficiency due to increased scattering, even for a low-angle diffuser having a FWHM of 5°.

Figure 4:
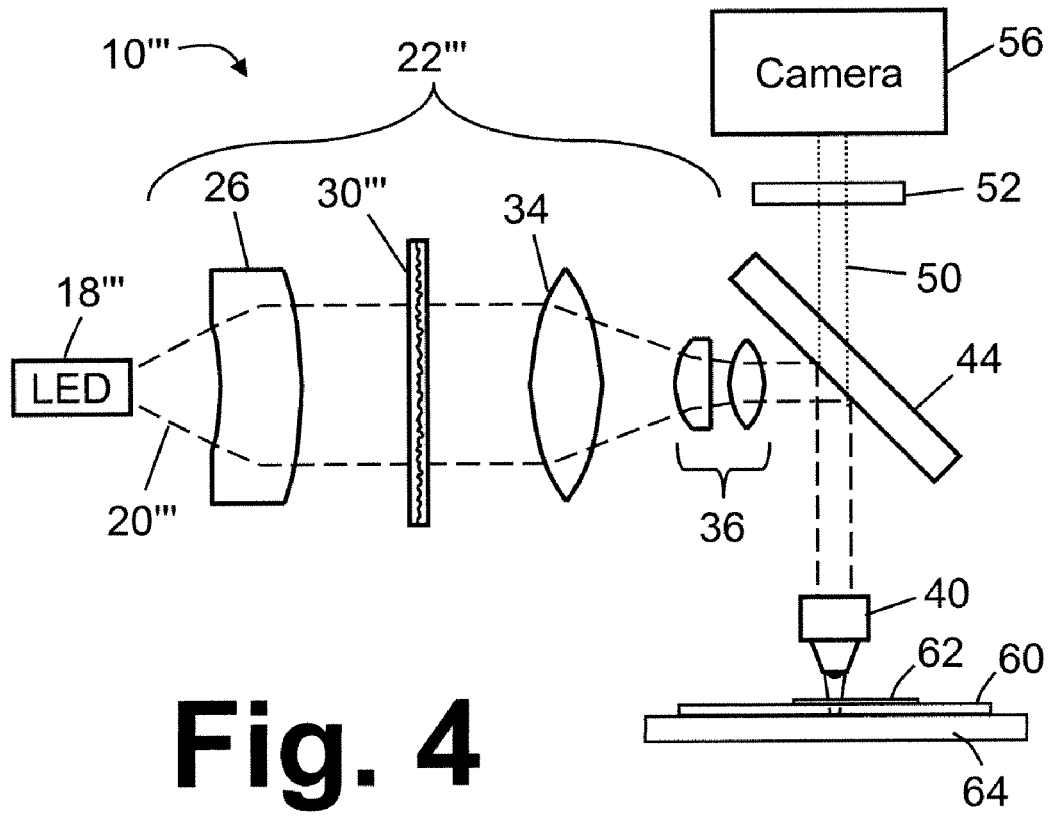
FIG. 4 diagrammatically shows the microscope system of FIG. 1 with yet another modified optical system.

With reference to FIG. 4, it is to be appreciated that the microscope systems disclosed herein are suitable for other microscopy applications besides imaging of samples contained in or supported by test tubes. In FIG. 4, a microscope system 10''' includes a light emitting diode (LED) 18''' as the light source, rather than the is laser 18 used in the previous microscope systems 10, 10', 10". Because the LED 18''' outputs diverging source light 20''' rather than a collimated laser beam, an optical train 22''' is modified in that the beam-expanding concave lens 24 is suitably omitted, as shown in FIG. 4. Alternatively, a lens can be included in the position of the lens 24, but selected to provide a suitable divergence angle adjustment for collimation by the collimating lens 26. The optical train 10''' employs a diffuser 30''' similar to the diffusers 30', 30''. The LED 18''' outputs incoherent light, and so speckle is generally not present. However, the output of the LED 18''' typically does have a non-Gaussian distribution, for example a Lambertian distribution. In view of these characteristics of the source light 20''', the diffuser 30''' is not tilted, and in some cases the diffuser 30''' can have a smaller divergence angle FWHM than the untilted diffuser 30' used to impart spatial uniformity to the laser beam source light 20 in the microscope system 10' of FIG. 2.

The microscope system 10''' of FIG. 4 further differs from the microscope systems 10, 10', 10'' in that the microscope system 10''' images a sample disposed on a planar slide 60, which is optionally covered by an optional cover glass 62. The slide 60 is disposed on an x-y planar translation stage 64 to enable scanning across the sample. It will be appreciated that the LED 18''' and optical train 22''' are also suitable for imaging the buffy coat sample disposed in the annular gap 12 between the light-transmissive test tube wall 14 and float wall 16 shown in FIGS. 1-3. Conversely, it will be appreciated that the laser 18 and optical train 22, 22', 22'' are also suitable for imaging the planar sample on the slide 60 shown in FIG. 4.

The optical trains 22, 22', 22'', 22''' have components which are stationary in the sense that the components are not rotated, relatively oscillated, or otherwise relatively moved. It is, however, contemplated to move the optical train and the objective 40 as a whole, and/or to include beam-steering elements, or so forth, to enable relative scanning of the field of view respective to the sample.

Suitable microscope systems for imaging an annular sample contained in or supported by a test tube have been described. The annular gap 12 typically has a thickness that is substantially larger than a depth of view of the microscope objective 40. The test tube wall 12 and float wall 16 are typically not uniform across the entire surface of the test tube or float. While the microscope objective 40 typically has an adjustable depth of focus (adjusted by moving internal optical components and/or by moving the objective 40 toward or away from the test tube wall 12), the range of adjustment is limited. Accordingly, the test tube should be held such that the surface proximate to the objective 40 is at a well-defined distance away from the objective 40 as the test tube is rotated and as the objective 40, or the test tube, is translated along a tube axis.

Suitable test tube holders for achieving such aspects are next described.

With reference to FIGS. 5-10, a test tube holder 70 has mounted therein a test tube 72 that is sealed by a test tube stopper 73. The sealed test tube 72 contains a float 74 and blood that has been suitably processed and centrifuged to separate out components including red blood cells, plasma, and a buffy coat, for example as described in U.S. Publ. Applications 2004/0067162 A1 and 2004/0067536 A1. The float 74 has a density which is less than that of the packed red blood cells component (1.090 g/ml) and greater than that of the plasma component (1.028 g/ml). Accordingly, after centrifuging the float 74 is disposed along the test tube axis 75 (drawn and labeled in FIG. 6) between the packed red blood cell layer and the plasma layer, that is, generally coincident with the buffy coat. After centrifuging, the buffy coat is generally disposed in the annular gap 12 between the test tube wall 14 and the float wall 16. (See labeling in FIG. 6). Annular sealing ridges 76, 78 at ends of the float 74 engage an inside surface of the test tube 72 when the test tube is at rest so as to seal the annular gap 12. During centrifuging, however, the test tube 72 expands to provide fluid communication across the ridges 76, 78 so as to enable the buffy coat to substantially collect in the annular gap 12.

At least one first alignment bearing, namely two radially spaced apart first alignment bearings 80, 81 in the example test tube holder 70, are disposed on a first side of the annular sampling region 12. At least one second alignment bearing, namely two second radially spaced apart alignment bearings 82, 83 in the example test tube holder 70, are disposed on a second side of the is annular sampling region 12 opposite the first side of the annular sampling region 12 along the test tube axis 75. The alignment bearings 80, 81, 82, 83 are fixed roller bearings fixed to a housing 84 by fastening members 85 (shown only in FIG. 8).

At least one biasing bearing, namely two biasing bearings 86, 87 in the example test tube holder 70, are radially spaced apart from the alignment bearings 80, 81, 82, 83 and are spring biased by springs 90 to press the test tube 72 against the alignment bearings 80, 81, 82, 83 so as to align a side of the annular sampling region 12 proximate to the objective 40 respective to the alignment bearings 80, 81, 82, 83. In the example test tube holder 70, the two first alignment bearings 80, 81 and the first biasing bearing 86 are radially spaced apart by 120° intervals and lie in a first common plane 92 on the first side of the annular sampling region 12. Similarly, the two second alignment bearings 82, 83 and the second biasing bearing 87 are radially spaced apart by 120° intervals and lie in a second common plane 94 on the second side of the annular sampling region 12. The springs 90 are anchored to the housing 84 and connect with the biasing bearings 86, 87 by members 98.

More generally, the bearings 80, 81, 86 and the bearings 82, 83, 87 may have radial spacings other than 120°. For example the biasing bearing 86 may be spaced an equal radial angle away from each of the alignment bearings 80, 81. As a specific example, the biasing bearing 86 may be spaced 135° away from each of the alignment bearings 80, 81, and the two alignment bearings 80, 81 are in this specific example spaced apart by 90°.

Optionally, the first common plane 92 also contains the float ridge 76 so that the bearings 80, 81, 86 press against the test tube 72 at the ridge 76, and similarly the second common plane 94 optionally also contains the float ridge 78 so that the bearings 82, 83, 87 press against the test tube 72 at the ridge 78. This approach reduces a likelihood of distorting the annular sample region 12. The biasing bearings 86, 87 provide a biasing force 96 that biases the test tube 72 against the alignment bearings 80, 81, 82, 83.

The housing includes a viewing window 100 that is elongated along the tube axis 75. The objective 40 views the side of the annular sample region 12 proximate to the objective 40 through the viewing window 100. In some embodiments, the objective 40 is linearly translatable along the test tube axis 75 as indicated by translation range double-arrow indicator 104. This can be accomplished, for example, by mounting the objective 40 and the optical train 22, 22', 22'', or 22''' on a common board that is translatable respective to the test tube holder 70. In another approach, the microscope system 10, 10', 10'', 10''' is stationary, and the tube holder 70 including the housing 84 is translated as a unit to relatively translate the objective 40 across the window 100. In yet other embodiments, the objective 40 translates while the optical train 22, 22', 22'', or 22''' remains stationary, and suitable beam-steering components (not shown, are provided to input the beam to the objective 40. The objective 40 is also focusable, for example by moving the objective 40 toward or away from the test tube 72 over a focusing range 106 (translation range 104 and focusing range 106 indicated only in FIG. 6).

Scanning of the annular sampling region 12 calls for both translation along the test tube axis, and rotation of the test tube 72 about the test tube axis 75. To achieve rotation, a rotational coupling 110 is configured to drive rotation of the test tube 72 about the tube axis 75 responsive to a torque selectively applied by a motor 112 connected with the rotational coupling 110 by a shaft 114. The rotational coupling 110 of the example test tube holder 70 connects with the test tube 72 at an end or base thereof. At an opposite end of the test tube 72, a spring-loaded cap 116 presses against the stopper 73 of the test tube 72 to prevent the rotation from causing concomitant translational slippage of the test tube 72 along the test tube axis 75.

Figure 9:
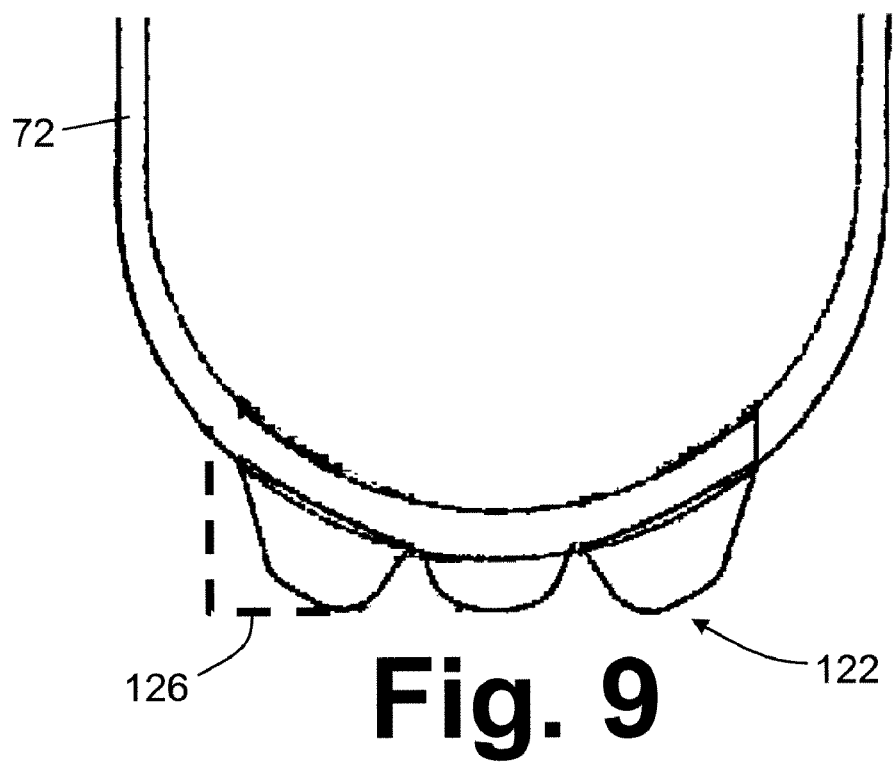
Figure 10:
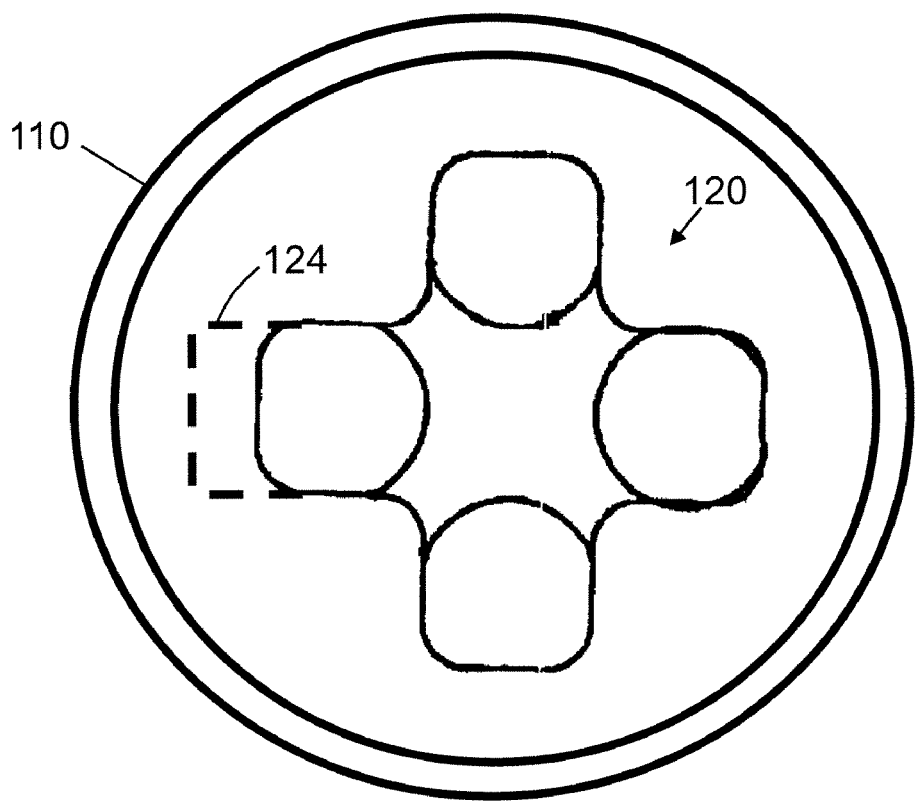

With particular reference to FIGS. 9 and 10, in some embodiments the rotational coupling 110 is a contoured coupling having a contour 120 configured to mate with a contoured base 122 of the test tube 72. In the illustrated example of FIGS. 9 and 10, the contour 120 of the coupling 110 includes four depressions that receive four nibs of the contoured base 122 of the test tube 72. Other contour features can be employed.

In some embodiments, the contour 120 and contoured base 122 are keyed by suitable rotationally asymmetric features 124, 126 (shown in phantom in FIGS. 9 and 10) in the coupling 110 and test tube base 122, respectively, to define an absolute rotational position of the test tube 72 when the contoured base 122 of the test tube 72 is mated with the contour 120 of the rotational coupling 110. In this way, the absolute rotational position (measured, for example as an absolute angle value in degrees) can be maintained even if the test tube 72 is removed from and then re-installed in the test tube holder 70.

In another approach for providing absolute angular position, the test tube optionally includes fiducial markers, for example optically readable reflective fiducial markers (not shown), to indicate the absolute rotational position of the test tube.

In some embodiments, the second side alignment roller bearings 82, 83 are omitted, and the rotational coupling 110 defines the at least one second alignment bearing disposed on the second side of the annular sampling region 12 opposite the first side of the annular sampling region 12 along the test tube axis 75. In such embodiments, the rotational coupling acts as a mechanically driven alignment bearing to provide both alignment and rotation of the test tube 72. Optionally, in such embodiments the second side bias bearing 87 is also omitted along with the corresponding roller bearings 82, 83.

On the other hand, in some other contemplated embodiments the rotational coupling 110 is omitted, and one or more of the roller bearings 81, 82, 83, 84, 86, 87 are mechanically driven to rotate the test tube 72. In such embodiments, the driven roller bearings serve as the rotational coupling. The driven bearings can be one or more of the alignment bearings 81, 82, 83, 84, or can be one or more of the biasing bearings 86, 87.

Figure 5:
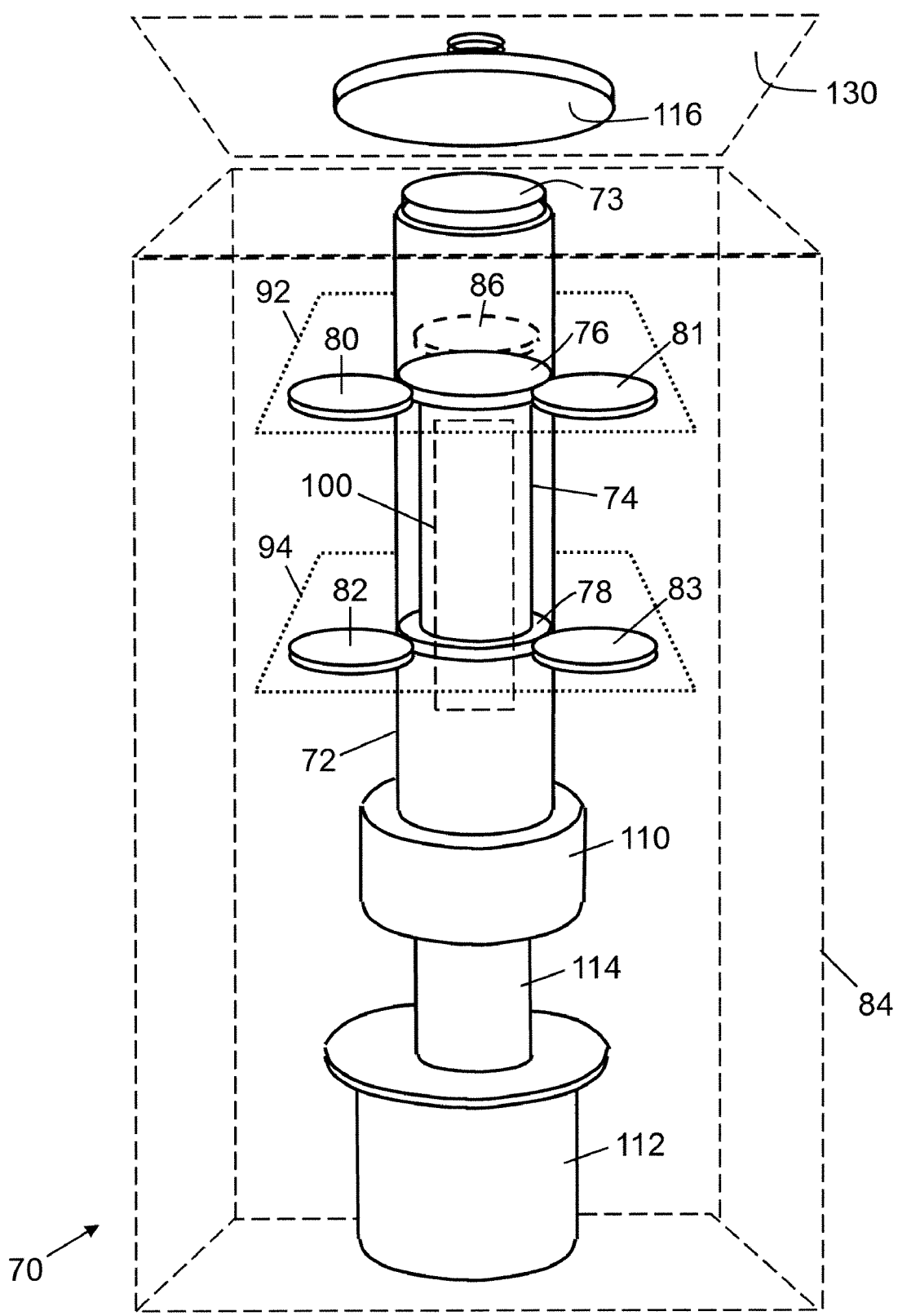
FIGS. 5-10 show various views of a test tube holder.
Figure 6:
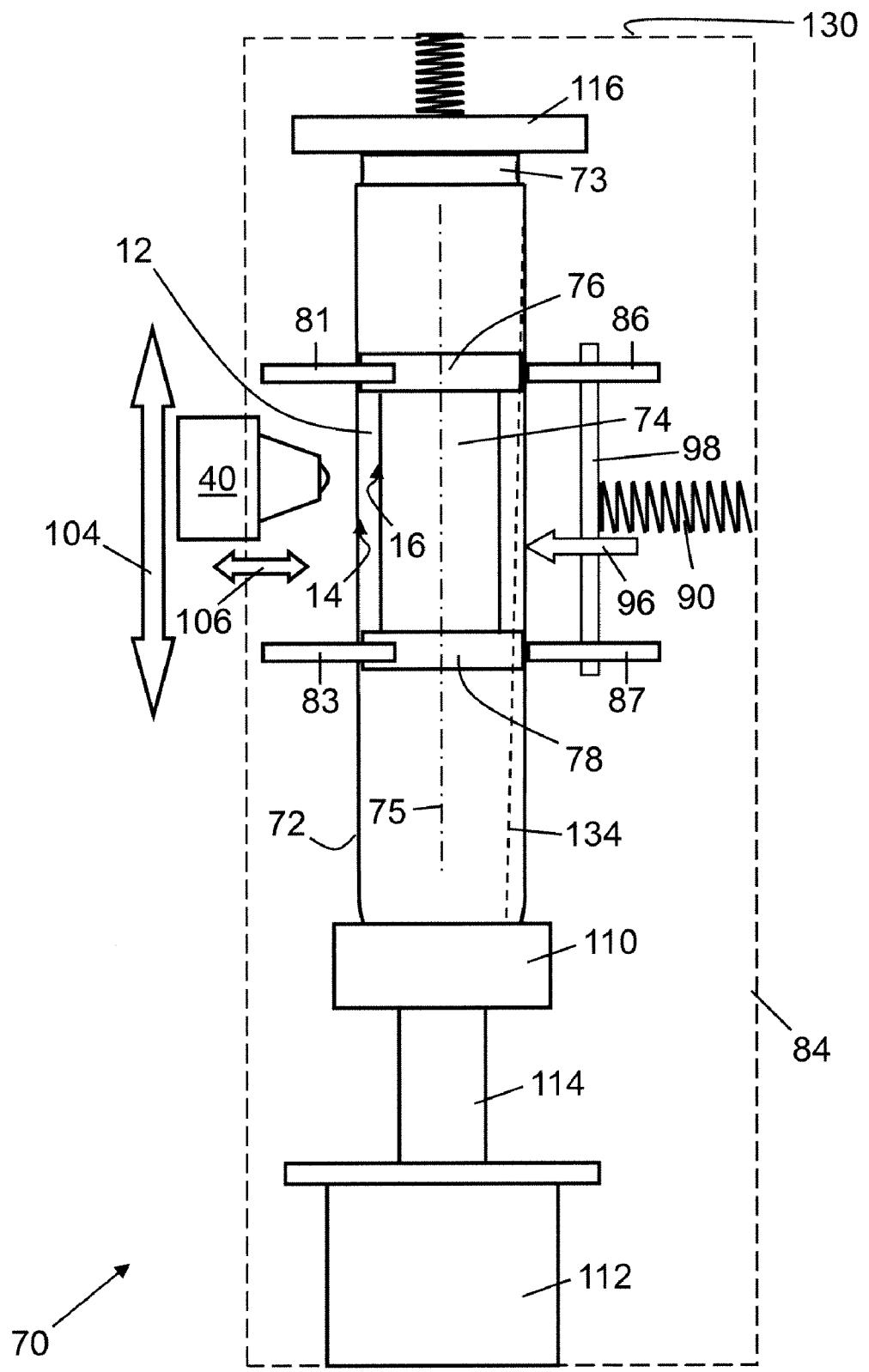
Figure 7:
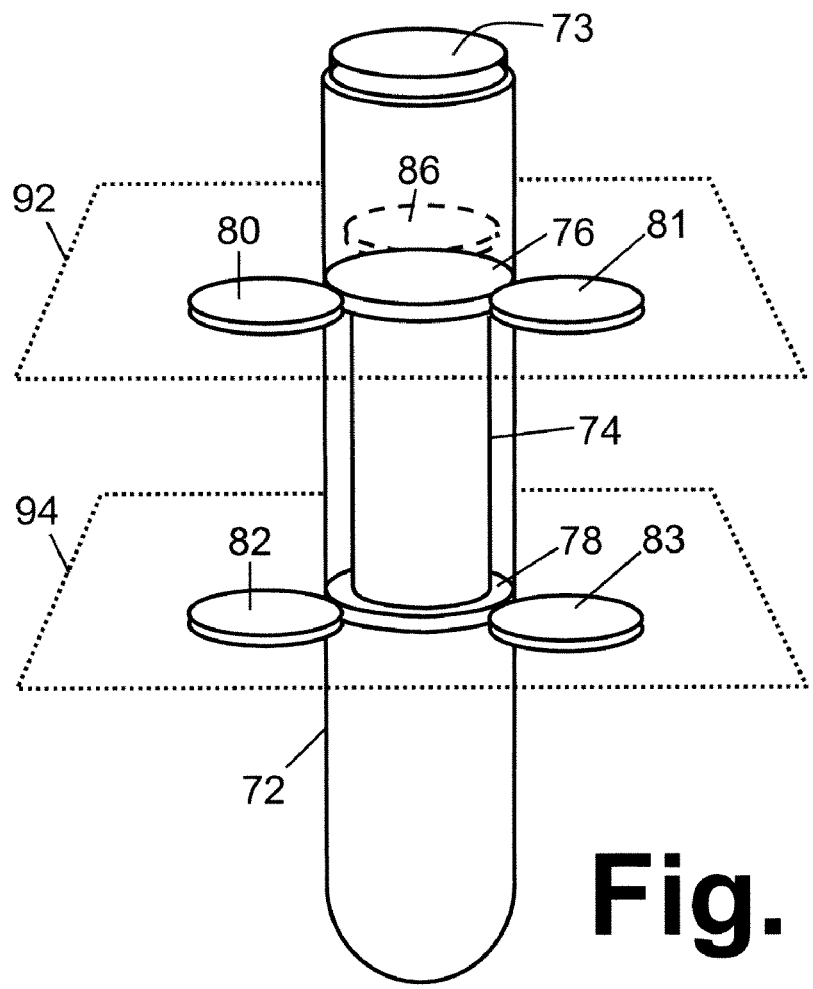
Figure 8:
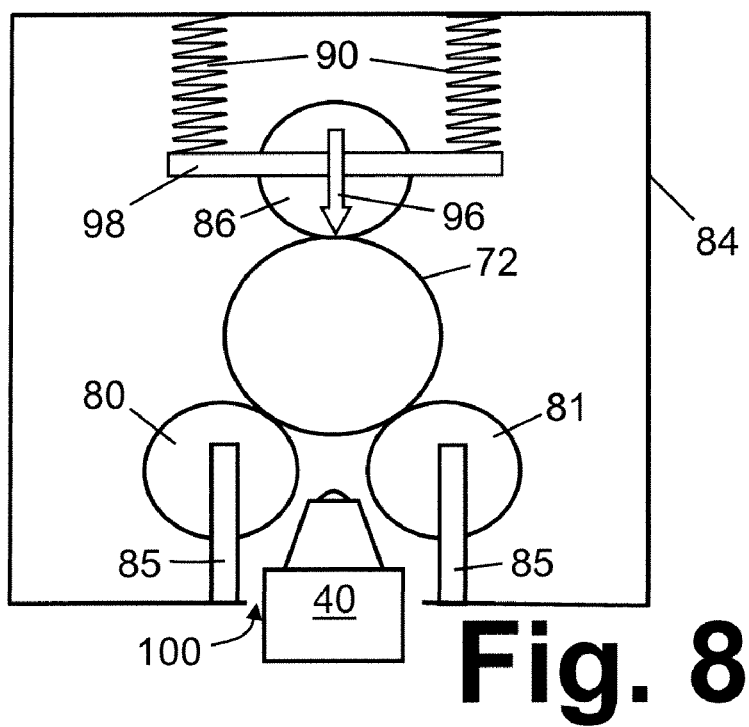

In order to install the test tube 72 in the test tube holder 70, the housing 84 is provided with a hinged lid or door 130 (shown open in FIG. 5 and closed in FIG. 6). When the hinged lid or door 130 is opened, the spring-loaded cap 116 is lifted off of the stopper 73 of the test tube 72. Optionally, the support members 98 that support the biasing bearings 86, 87 include a manual handle or lever (not shown) for manually drawing the biasing bearings 86, 87 away from the test tube 72 against the biasing force of the springs 90 so as to facilitate loading or unloading the test tube 72 from the holder 70.

The test tube holder 70 advantageously can align the illustrated test tube 72 which has straight sides. The test tube holder 70 can also accommodate and align a slightly tapered test tube. The held position of a tapered test tube is indicated in FIG. 6 by a dashed line 134 which indicates the tapered edge of a tapered test tube. The illustrated tapering 134 causes the end of the test tube closest to the rotational coupling 110 to be smaller diameter than the end of the test tube closest to the spring-loaded cap 116. As indicated in FIG. 6, the biasing of the biasing bearings 86, 87 presses the test tube against the alignment bearings 81, 82, 83, 84 to maintain alignment of the portion of the annular sample region 12 proximate to the objective 40 in spite of the tapering 134. It will be appreciated that the holder 70 can similarly accommodate and align a test tube having an opposite taper in which the end closes to the rotational coupling 110 is larger in diameter than the end closest to the spring-loaded cap 116.

In the case of a substantial tapering, or in the case a test tube that has a highly eccentric or non-circular cross-section, the biasing against the alignment bearings 81, 82, 83, 84 will not completely compensate for the tapering or cross-sectional eccentricity or ellipticity. This is because the radial spacing apart of the first alignment bearings 81, 82 and the radial spacing apart of the second alignment bearings 83, 84 allows a narrower tube to extend a further distance into the gap between the first alignment bearings 81, 82 and into the gap between the second alignment bearings 83, 84.

Figure 11A:
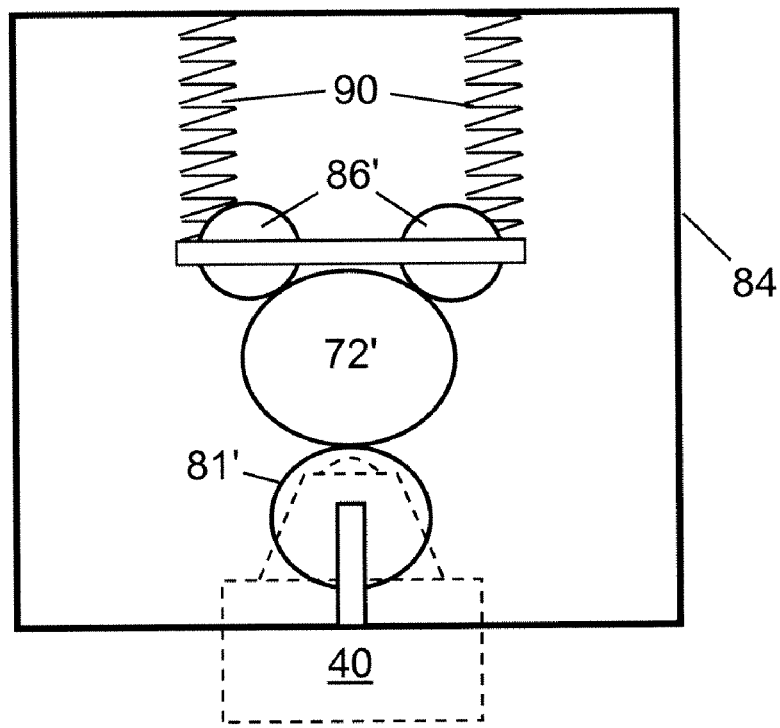
FIGS. 11A and 11B show top views of another embodiment test tube holder, with a test tube having an eccentric cross-section loaded.
Figure 11B:
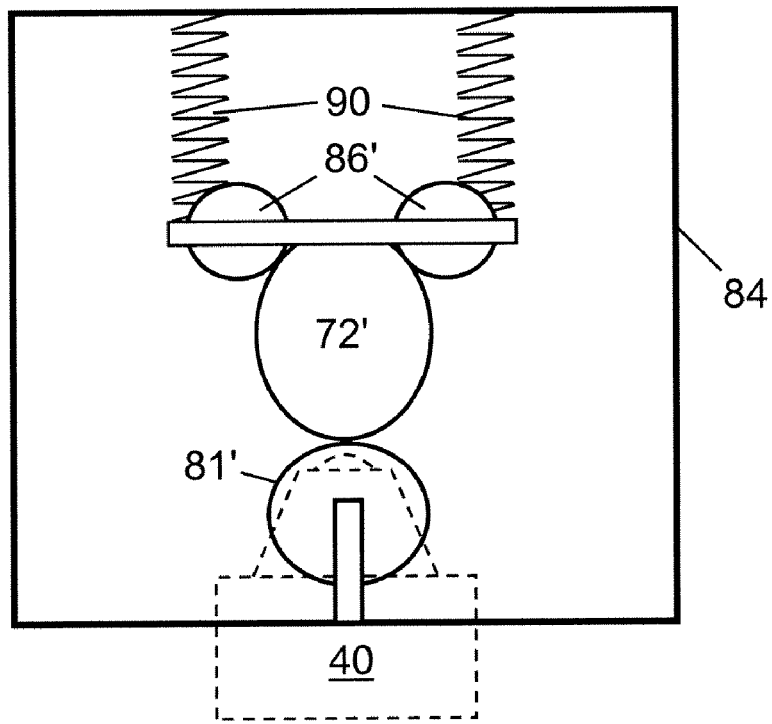

With reference to FIGS. 11A and 11B, a modified test tube 72' having an elliptical cross-section is more precisely aligned by employing a set of three bearings per supported float ridge, in which the three bearings include only one alignment bearing 81' and two or more biasing bearings 86'. The alignment bearing 81' is at the same radial position as the objective 40 (shown in phantom in FIGS. 11A and 11B). As the elliptical test tube 12' rotates, the imaged side that is biased against the alignment bearings 81' remains precisely aligned with the radially coincident objective 40 whether the imaged side correspond to the short axis of the elliptical test tube 72' (FIG. 11A), or whether the imaged side correspond to the long axis of the elliptical test tube 72' (FIG. 11B).

Figure 12:
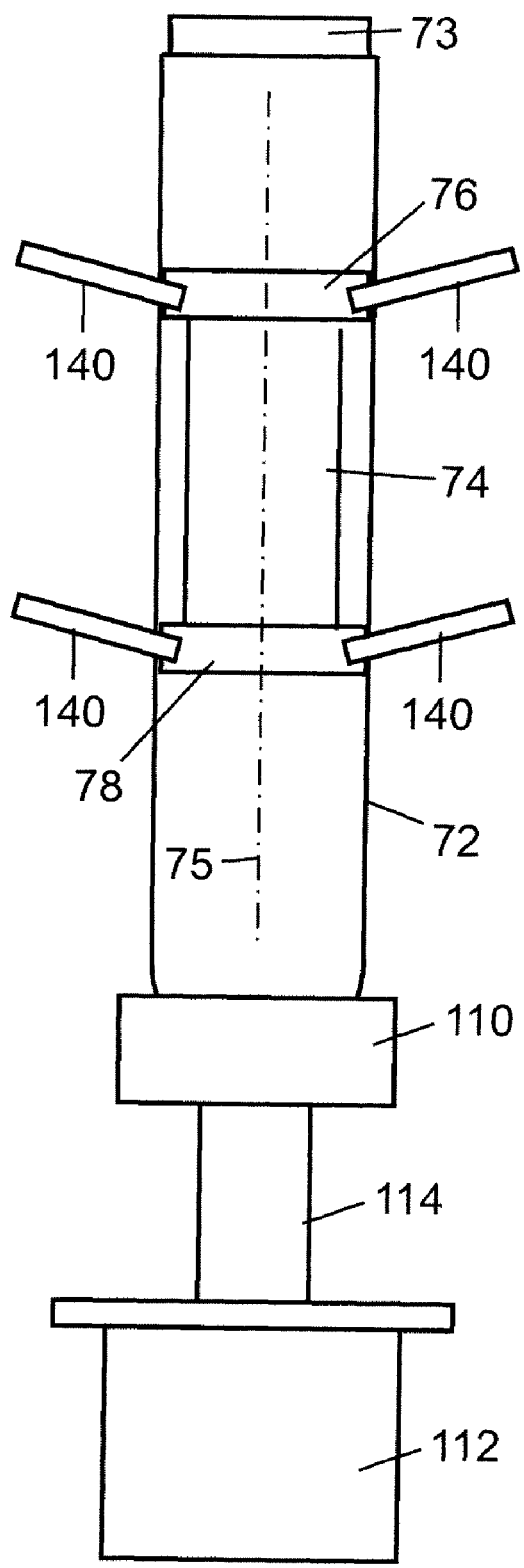
FIG. 12 shows a side view of a portion of a test tube holder employing tilted roller bearings.

With reference to FIG. 12, in another variation, bearings 140 are tilted respective to the tube axis 75 of the test tube 72 to impart force components parallel with the tube axis 75 to push the test tube 72 into the rotational coupling 110. In this arrangement, the spring-loaded cap 116 is optionally omitted, because the tilting of the bearings 140 opposes translational slippage of the test tube 72 during rotation.

Figure 13:
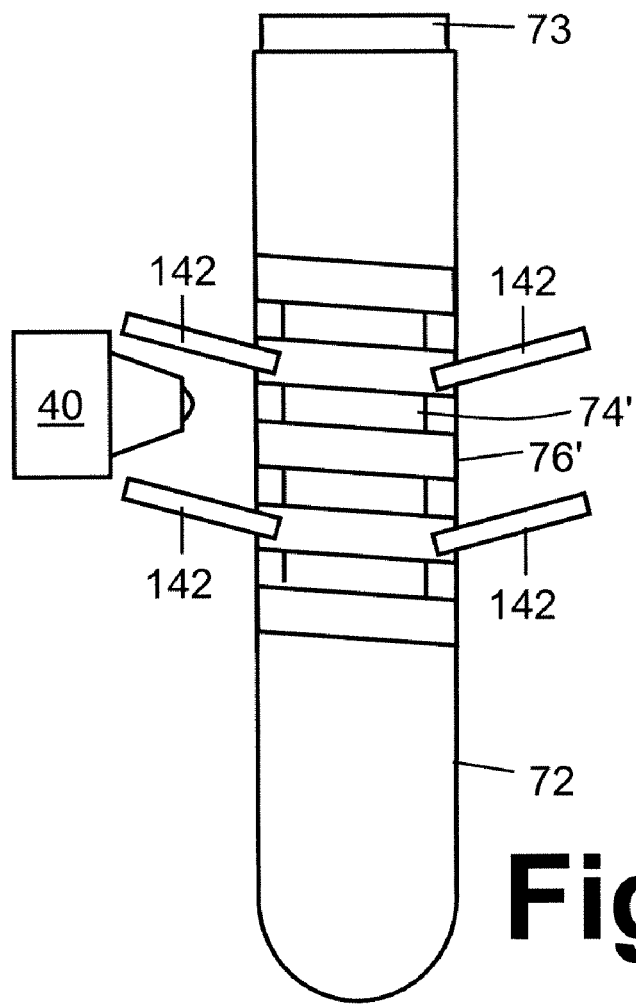
FIG. 13 shows a side view of a portion of a test tube holder employing tilted roller bearings staggered along a test tube axis, along with a float having helical ridges enables spiral scanning of the test tube.

With reference to FIG. 13, in another variation, a modified float 74' includes spiral ridges 76', and tilted bearings 142 are spaced along the tube axis 75 in accordance with the spiral pitch to track the spiraling sealing ridges 76' responsive to rotation of the test tube 72. In this approach, the tilted bearings 142 impart a force that causes the test tube 72 to translate along the tube axis 75, so that the objective 40 can be maintained at a fixed position without translating while scanning annular gap 12'. In this approach, the roller bearings 142 are suitably motorized to generate rotation of the test tube 72. That is, the roller bearings 142 also serve as is the rotational coupling.

Figure 14:
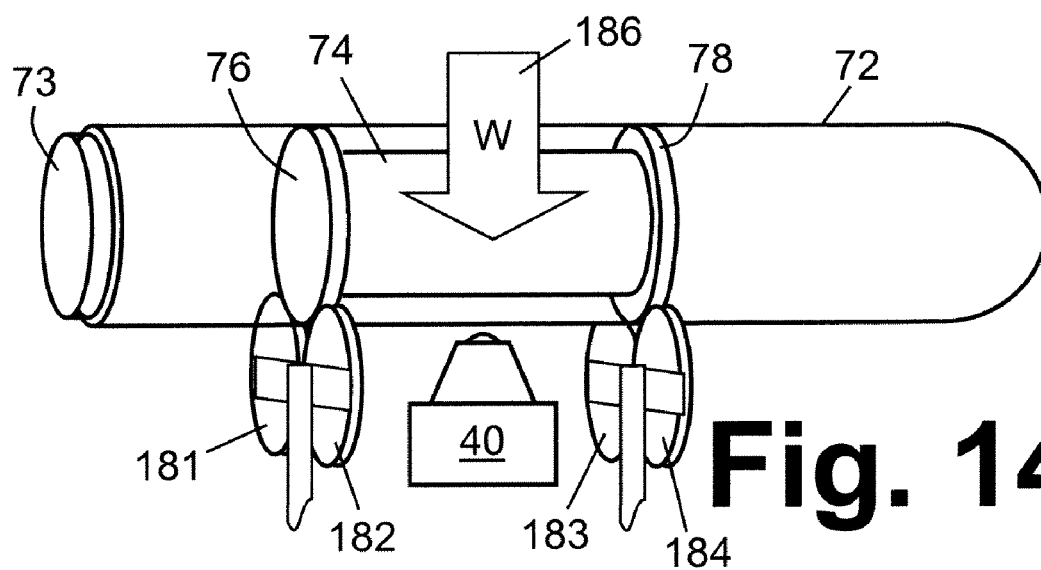
FIG. 14 shows a perspective view of a test tube holder that holds the test tube horizontally and uses the test tube as a bias force.

With reference to FIG. 14, in another variation, the mechanical bias can be provided by a mechanism other than biasing bearings. In example FIG. 14, the test tube 72 is arranged horizontally resting on alignment bearings 181, 182, 183, 184 with the objective 40 mounted beneath the test tube 72. A weight 186 of the test tube 72 including the float 74 (said weight diagrammatically indicated in FIG. 14 by a downward arrow 186) provides as the mechanical bias pressing the test tube 72 against the alignment bearings 181, 182, 183, 184. In other contemplated embodiments, a vacuum chuck, positive air pressure, magnetic attraction, or other mechanical bias is employed to press the test tube against the alignment bearings. The alignment bearings 181, 182, 183, 184 can be rotated mechanically so that the alignment bearings 181, 182, 183, 184 serve as the rotational coupling, or a separate rotational coupling can be provided.

Figure 15:
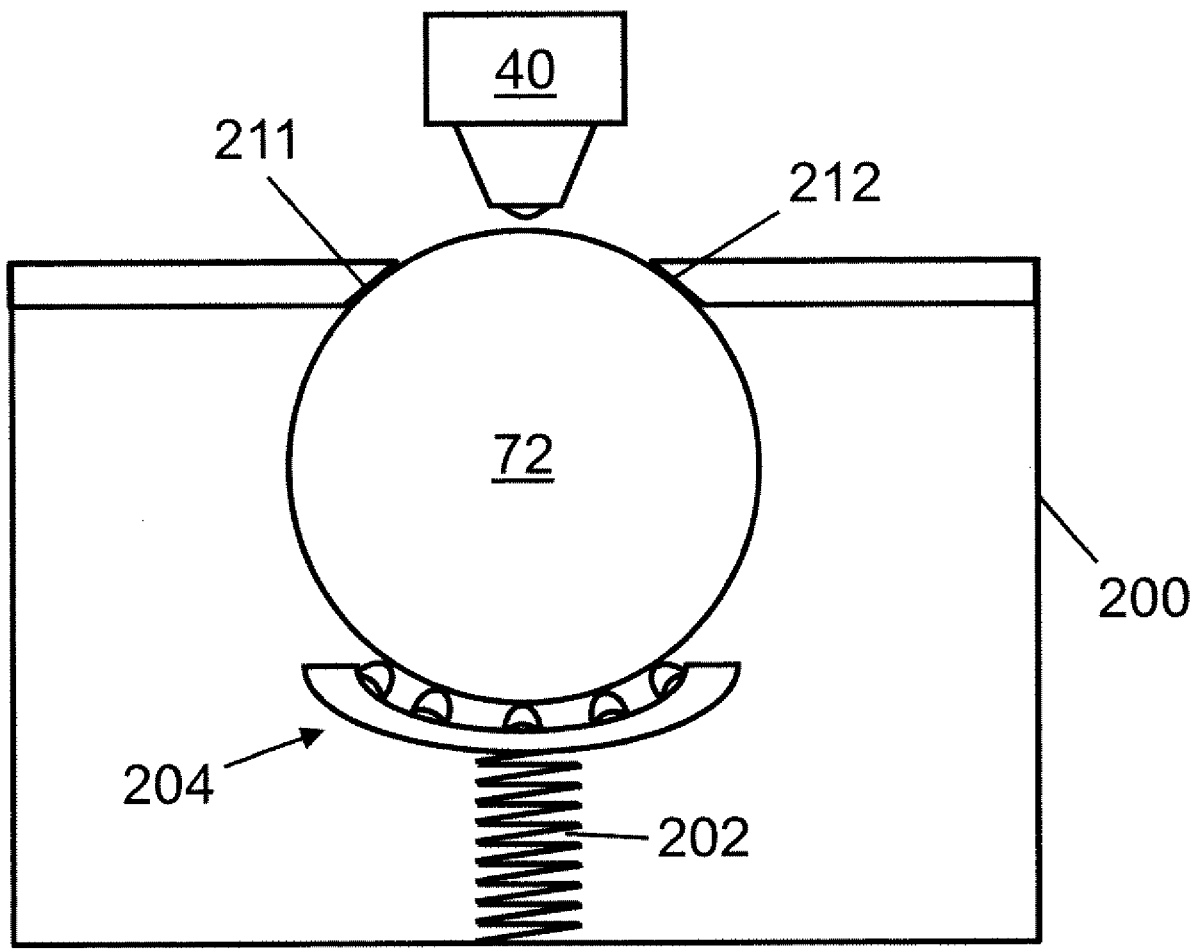
FIG. 15 shows a top view of a test tube holder employing bushing surfaces as alignment bearings and a set of ball bearings as bias bearings.

With reference to FIG. 15, the bearings can be other than roller bearings. For example, the bearings can be rollers, ball bearings, or bushing surfaces. In the variant test tube holder shown in FIG. 15, a housing 200 provides an anchor for a spring 202 that presses a set of biasing ball bearings 204 against the test tube 72 to press the test tube 72 against alignment bearings 211, 212 defined by bushing surfaces of the housing 200. Other types of bearings can be used for the biasing and/or alignment bearings that support the test tube as it rotates.

In the illustrated embodiments other than the embodiment of FIG. 13, the test tube is not translated within the tube holder, and instead the translative component of the scanning is achieved by translating the objective 40, or by translating the test tube and tube holder as a unit. In other contemplated embodiments, it is contemplated to keep the objective fixed and to translate the test tube within the test tube housing, for example by including a linear translation capability in the shaft 114 connecting the motor 112 with the rotational coupling 112 so as to translate the test tube 72 along the test tube axis 75.

Suitable microscope systems and test tube holders have been described for imaging an annular sample region contained in or supported by a test tube. It is to be understood that the annular sampling region can be other than the illustrated fluid sample contained in the gap 12 between the test tube wall 14 and the float wall 16. For example, the annular sample region can be a film or coating adhered on an outside surface of the test tube, or the annular sample region can be a film or coating adhered on an inside surface of the test tube. Moreover, the term "test tube" is to be broadly construed as encompassing other tubular sample holders besides the illustrated conventional test tube 72. For example, the test tube could be a cylindrical rod that has been inserted into a contained volume, solid object, or other subject of interest so as to coat an outside of the cylindrical rod with a sample of the subject of interest, or the test tube can be a cylindrical geological core sample, or so forth.

Having described suitable microscope systems and test tube holders for acquiring data from an annular slide or annular sampling region contained in or supported by a test tube, suitable processing approaches for identifying or quantifying fluorescent dye tagged cells in an annular biological fluid layer are now described.

Figure 16:
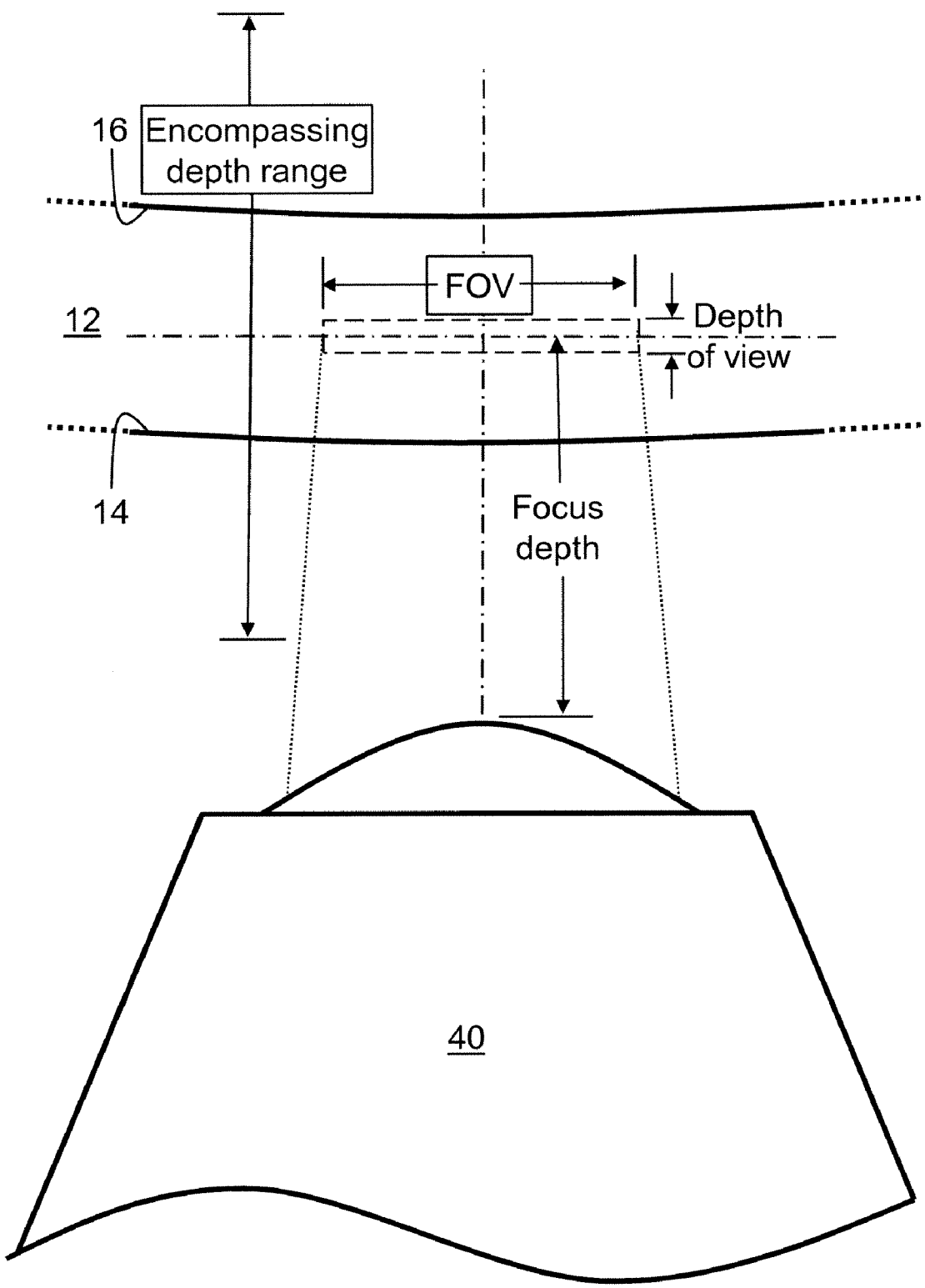
FIG. 16 diagrammatically depicts certain measurement parameters relevant in performing quantitative buffy coat analysis using a buffy coat sample trapped in an annular gap between an inside test tube wall and an outer surface of a float.

With reference to FIG. 16, certain measurement parameters are diagrammatically illustrated. The objective 40 images over a field of view (FOV) and over a depth of view located at a focus depth. In FIG. 16, the focus depth is indicated respective to the objective 40; however, the focus depth can be denoted respective to another reference. In some embodiments, the depth of view of the objective 40 is about 20 microns, while the annular gap 12 between the test tube wall 14 and the float wall 16 is about 50 microns. However, the depth of focus corresponding to the annular gap 12 can vary substantially due to non-uniformities in the test tube and/or the float or other factors. It is expected that the annular gap 12 is located somewhere within an encompassing depth range. In some embodiments, an encompassing depth range of 300 microns has been found to be suitable. These dimensions are examples, and may be substantially different for specific embodiments depending upon the specific objective 40, light-transmissive test tube, float, the type of centrifuging or other sample processing applied, and so forth.

Figure 17:
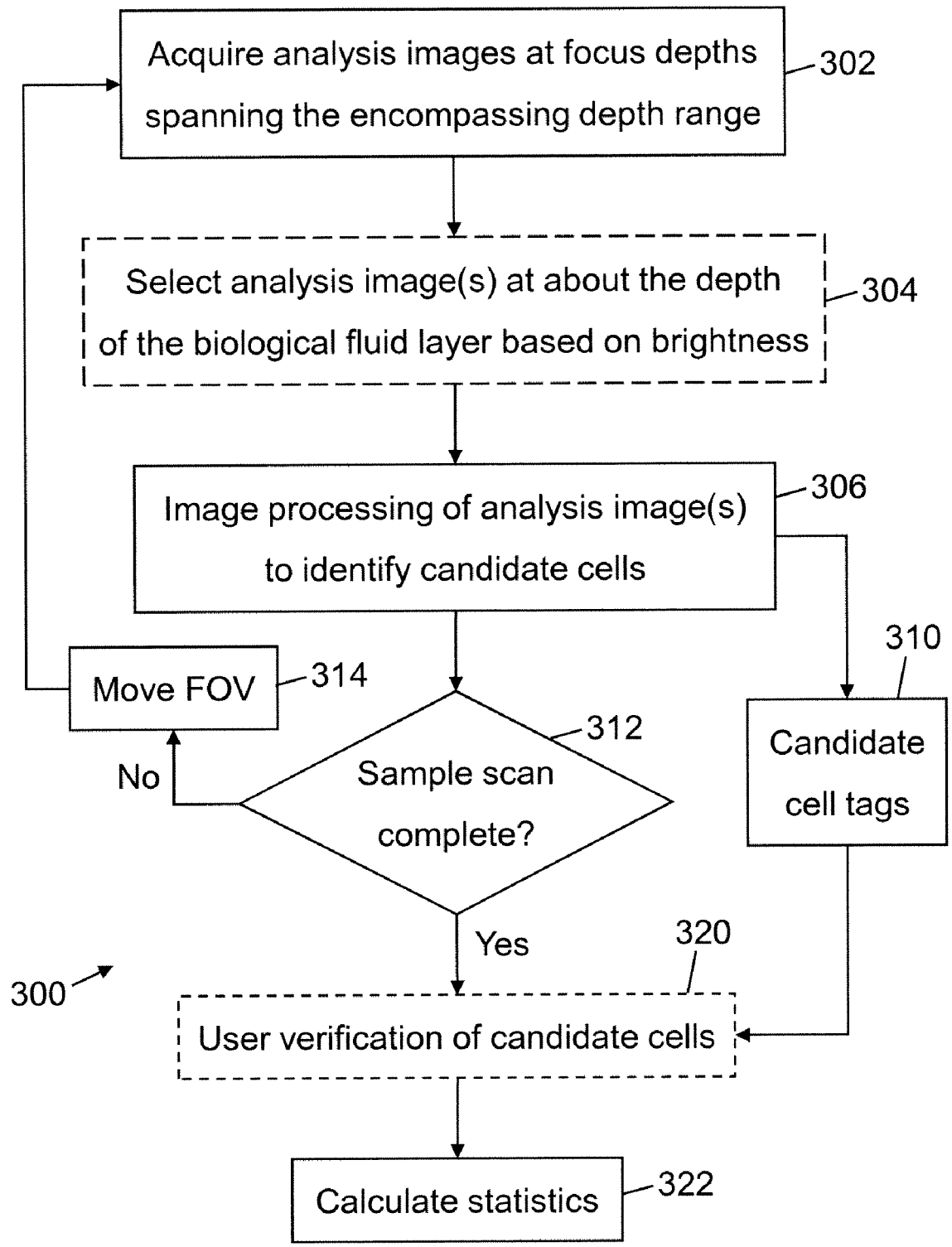
FIG. 17 diagrammatically shows a suitable quantitative buffy coat measurement/analysis approach.

With reference to FIG. 17, one suitable data acquisition approach 300 is diagrammatically shown. In process operation 302, analysis images are acquired at a plurality of focus depths spanning the encompassing depth range. To avoid gaps in the depth direction, the number of analysis images acquired in the operation 302 should correspond to at least the encompassing depth range divided by the depth of view of the objective 40.

In some embodiments, the analysis images are processed in optional operation 304 to identify one or more analysis images at about the depth of the biological fluid layer (such as the buffy layer) based on image brightness. This optional selection takes advantage of the observation that typically the fluorescent dye produces a background fluorescence that is detected in the acquired analysis images as an increased overall image brightness. Image brightness can be estimated in various ways, such as an average pixel intensity, a root-mean-square pixel intensity, or so forth.

In an image processing operation 306, the analysis images, or those one or more analysis images selected in the optional selection operation 304, are processed using suitable techniques such as filtering, thresholding, or so forth, to identify observed features as candidate cells. The density of dye-tagged cells in the biological fluid layer is typically less than about one dye-tagged cell per field of view. Accordingly, the rate of identified candidate cells is typically low. When a candidate cell is identified by the image processing 306, a suitable candidate cell tag is added to a set of candidate cell tags 310. For example, a candidate cell tag may identify the image based on a suitable indexing system and x- and y-coordinates of the candidate cell feature. Although the density of rare cells is typically low, it is contemplated that the image processing 306 may nonetheless on occasion identify two or more candidate cells in a single analysis image. On the other hand, in some analysis images, no candidate cells may be identified.

At a decision point 312, it is determined whether the sample scan is complete. If not, then the field of view is moved in operation 314. For example, the field of view can be relatively scanned across the biological fluid sample in the annular gap 12 by a combination of rotation of the test tube 72 and translation of the objective 40 along the test tube axis 75. Alternatively, using the tube holder of FIG. 13, scanning is performed by moving the test tube 72 spirally. For each new field of view, the process operations 302, 304, 306 are repeated.

Once the decision point 312 indicates that the sample scan is complete, a user verification process 320 is optionally employed to enable a human analyst to confirm or reject each cell candidacy. If the image processing 306 is sufficiently accurate, the user verification process 320 is optionally omitted.

A statistical analysis 322 is performed to calculate suitable statistics of the cells confirmed by the human analyst. For example, if the volume or mass of the biological fluid sample is known, then a density of rare cells per unit volume or per unit weight (e.g., cells/milliliter or cells/gram) can be computed. In another statistical analysis approach, the number of confirmed cells is totaled. This is a suitable metric when a standard buffy sample configuration is employed, such as a standard test tube, standard float, standard whole blood sample quantity, and standardized centrifuging processing. The statistical analysis 322 may also include threshold alarming. For example, if the cell number or density metric is greater than a first threshold, this may indicate a heightened possibility of cancer calling for further clinical investigation, while if the cell number or density exceeds a second, higher threshold this may indicate a high probability of the cancer calling for immediate remedial medical attention.

Figure 18:
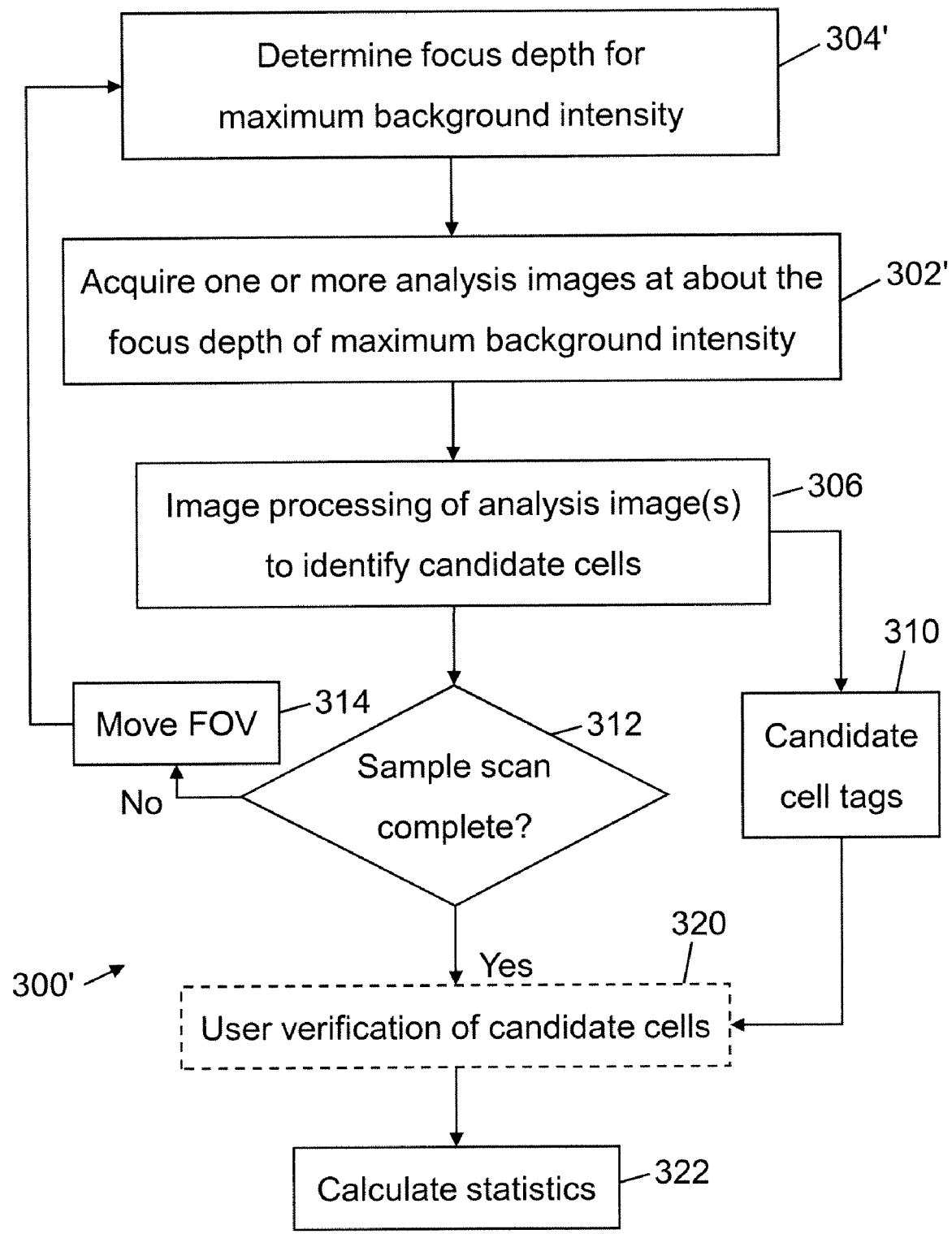
FIG. 18 diagrammatically shows another suitable quantitative buffy coat measurement/analysis approach.

With reference to FIG. 18, a modified acquisition approach 300' is diagrammatically shown. In modified process operation 304', the focus depth for maximum background fluorescence intensity is first determined using input other than analysis images, followed by acquisition 302' of one or a few analysis images at about the focus depth for maximum background fluorescence. For example, the search process 304' can be performed by acquiring low resolution images at various depths. To avoid gaps in the depth direction, the number of low resolution images acquired in the operation 304' should correspond to at least the encompassing depth range divided by the depth of view of the objective 40. In another approach, a large-area brightness sensor (not shown) may be coupled to the captured fluorescence 50 (for example, using a partial mirror in the camera 56, or using an intensity meter built into the camera 56) and the focus of the objective 40 swept across the encompassing depth range. The peak signal of the sensor or meter during the sweep indicates the focus providing highest brightness.

With the depth of the biological fluid sample determined by the process operation 304', the acquisition process 302' acquires only one or a few analysis images at about the identified focus depth of highest brightness. To ensure full coverage of the biological fluid layer, the number of acquired analysis images should be at least the thickness of the annular gap 12 divided by the depth of view of the objective 40. For example, if the annular gap 12 has a thickness of about 50 microns and the depth of view is about 20 microns, then three analysis images are suitably acquired—one at the focus depth of highest brightness, one at a focus depth that is larger by about 15-25 microns, and one at a focus depth that is smaller by about 15-25 microns.

An advantage of the modified acquisition approach 300' is that the number of acquired high resolution analysis images is reduced, since the focus depth is determined prior to acquiring the analysis images. It is advantageous to bracket the determined focus depth by acquiring analysis images at the determined focus depth and at slightly larger and slightly smaller focus depths. This approach accounts for the possibility that the rare cell may be best imaged at a depth that deviates from the depth at which the luminescence background is largest.

Figure 19:
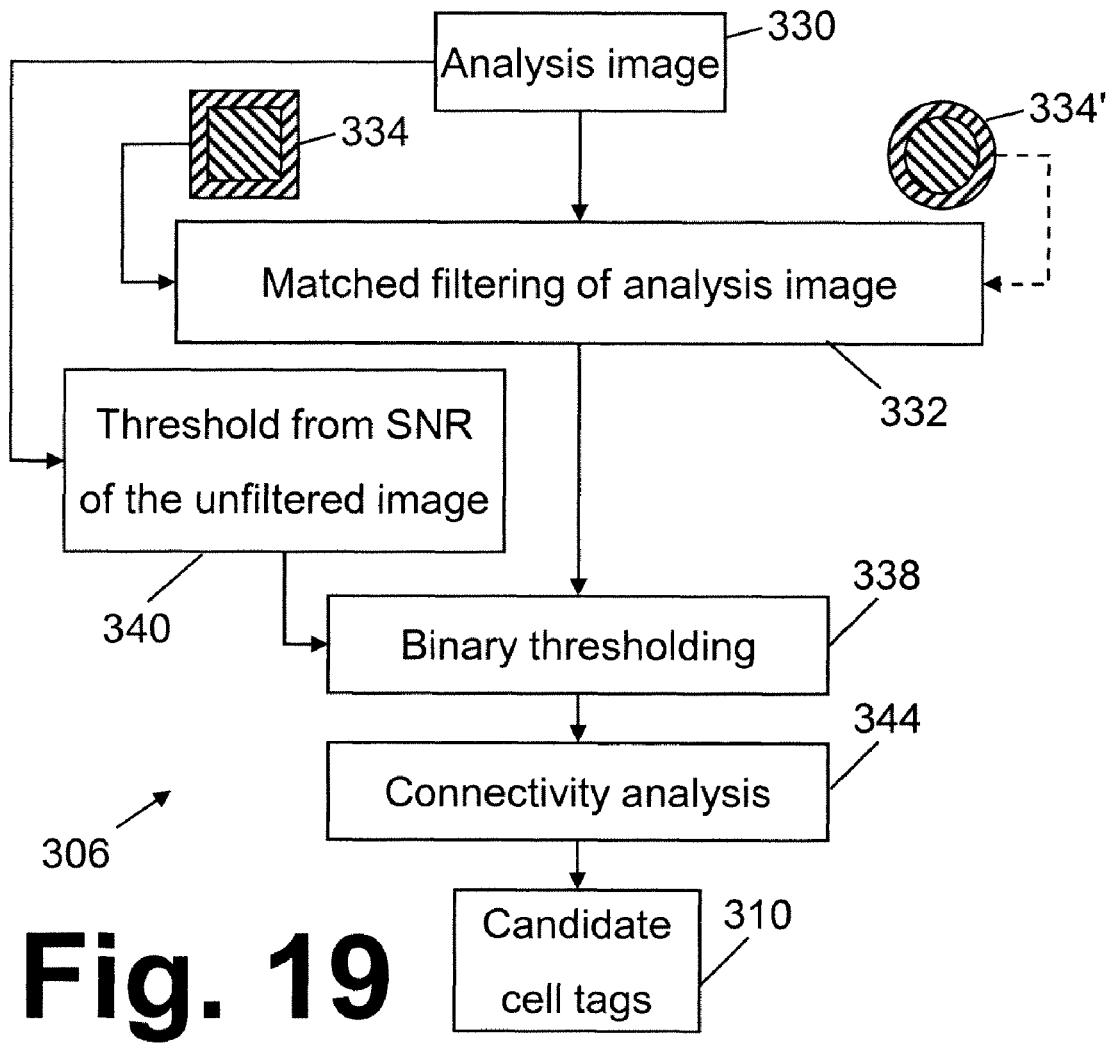
FIG. 19 diagrammatically shows a suitable image processing approach for tagging candidate cells.

With reference to FIG. 19, a suitable embodiment of the image processing 306 is described, which takes advantage of a priori knowledge of the expected rare cell size to identify any cell candidates in an analysis image 330. In a matched filtering process 332, a suitable filter kernel is convolved with the image. The matched filtering 332 employs a filter kernel having a size comparable with the expected size of an image of a rare cell in the analysis image 330.

Figures 20, 21:
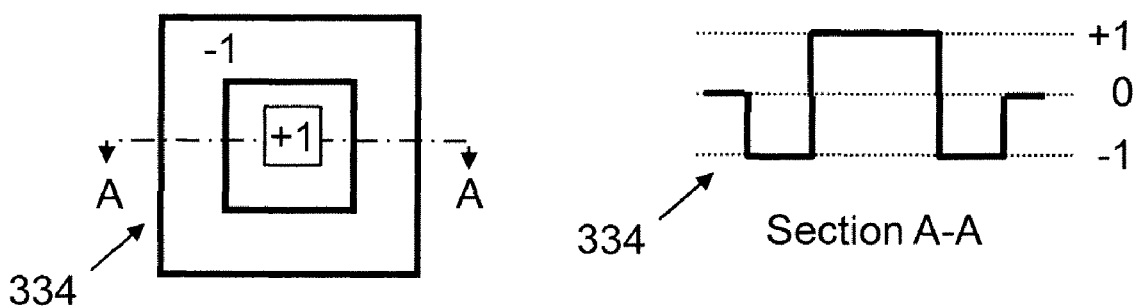
FIG. 20 shows a pixel layout for a square filter kernel suitable for use in the matched filtering.
FIG. 21 shows a pixel intensity section A-A of the square filter kernel of FIG. 20.

With continuing reference to FIG. 19 and with brief further reference to FIGS. 20 and 21, in some embodiments a square filter kernel 334 is employed. The kernel 334 includes a central positive region of pixels each having a value of +1, and an outer negative region of pixels each having a value of −1. The area of the positive region should be about the same size as the area of the negative region. Points outside of either the inner or outer region have pixel values of zero. Optionally, other pixel values besides +1 and −1 can be used for the inner and outer regions, respectively, so as to give the filter is a slightly positive or slightly negative response.

With continuing reference to FIG. 19, the matched filtering removes or reduces offsets caused by background illumination, and also improves the signal-to-noise ratio (SNR) for rare cells. The signal is increased by the number points in the positive match area, while the noise is increased by the number of points in both the positive and negative match areas. The gain in SNR comes from the fact that the signal directly adds, while the noise adds as the root-mean-square (RMS) value or as the square root of the number of samples combined. For a filter with N positive points and N negative points, a gain of $N/\sqrt{(2N)}$ or $\sqrt{(N/2)}$ is obtained.

The square filter kernel 334 is computationally advantageous since its edges align with the x- and y-coordinate directions of the analysis image 330. A round filter kernel 334' or otherwise-shaped kernel is optionally used in place of the square filter kernel 334. However, the round filter kernel 334' is more computationally expensive than the square filter kernel 334. Another advantage of the square filter kernel 334 compared with the round filter kernel 334' is that the total filter edge length of the square filter 334 is reduced from twice the detection size to 1.414 times the detection size. This reduces edge effects, allowing use of data that is closer to the edge of the analysis image 330.

The size of the filter kernel should be selected to substantially match the expected image size of a dye-tagged cell in the analysis image 330 to provide the best SNR improvement. For example, the square filter kernel 334 with a positive (+1) region that is ten pixels across is expected to provide the best SNR improvement for a cell image also having a diameter of about ten pixels. For that matched case, the signal is expected to increase by about a factor of 78 while the noise is expected to increase by about a factor of 14, providing a SNR improvement of about 5.57:1. On the other hand, the SNR improvement for a smaller eight pixel diameter cell using the same square filter is expected to be about 3.59:1. The SNR improvement for a larger fourteen pixel diameter cell using the same square filter is expected to be about 3.29:1.

The matched filter processing 332 can be implemented in various ways. In one approach, each point in the input image is summed into all points in the output image that are in the positive inner region. Then all the points in the output image that are in the outer negative region but not in the inner positive region are subtracted off. Each point in the input image is touched once, while each point in the output image is touched the outer-box pixel area count number of times.

In another suitable approach, for each point in the output image, all points from the input image that are within the positive inner box are read and summed. All points outside the positive inner box but within the negative outer box are then subtracted. While each output image pixel is touched only once, each input image pixel is touched by the outer-box pixel count.

In another suitable approach, two internal values are developed for the current row of the input image: a sum of all points in the row in the negative outer box distance, and a sum of all points in the row in the inner positive box distance. All output image column points at the current row have the input image sum of all points in the outer-box subtracted from them. All the output image column points within the inner positive box get the sum of the input image row points in the inner positive box distance added in twice. The row sums can be updated for the next point in the row by one add and one subtract. This reduces the execution cost to be on the order of the height of the filter box.

In the matched filter processing 332, various edge conditions can be employed. For example, in one approach, no output is produced for any point whose filter overlaps an edge of the analysis image 330. This approach avoids edge artifacts, but produces an output image of reduced usable area. In another suitable example edge condition, a default value (such as zero, or a computed mean level) is used for all points off the edge.

With continuing reference to FIG. 19, binary thresholding processing 338 is applied after the matched filtering 332. A difficulty in performing the thresholding 338 is selection of a suitable threshold value. Threshold selection is complicated by a likelihood that some analysis images will contain no cells, or only a single cell, or only a couple or few cells. In one approach, a the threshold is selected as a value that is a selected percentage below the peak pixel intensity seen in the filtered data. However, this threshold will cause noise to be detected when no cells are present, since in that case the peak pixel value will be in the noise. Another approach is to use a fixed threshold. However, a fixed threshold may be far from optimal if the background intensity varies substantially between analysis images, or if the matched filtering substantially changes the dynamic range of the pixel intensities.

In the illustrated approach, the threshold is determined by processing 340 based on the SNR of the unfiltered analysis image 330. By first determining the standard deviation of the input image, the expected noise at the filter output can be computed. The noise typically rises by the square root of the number of pixels summed, which is the outer-box area in pixel counts. In some embodiments, the threshold is set at approximately 7-sigma of this noise level. As this filter does not have an exact zero DC response, an appropriate mean level is also suitably summed to the threshold.

The thresholding 338 produces a binary image in which pixels that are part of a cell image generally have a first binary value (e.g., "1") while pixels that are not part of a cell image generally have second binary value (e.g., "0"). Accordingly, connectivity processing 344 is performed to identify a connected group of pixels of the first binary value corresponding to a cell. The connectivity analysis 344 aggregates or associates all first binary value pixels of a connected group as a cell candidate to be examined as a unit. The center of this connected group or unit can be determined and used as the cell location coordinates in the candidate cell tag.

Figure 22:
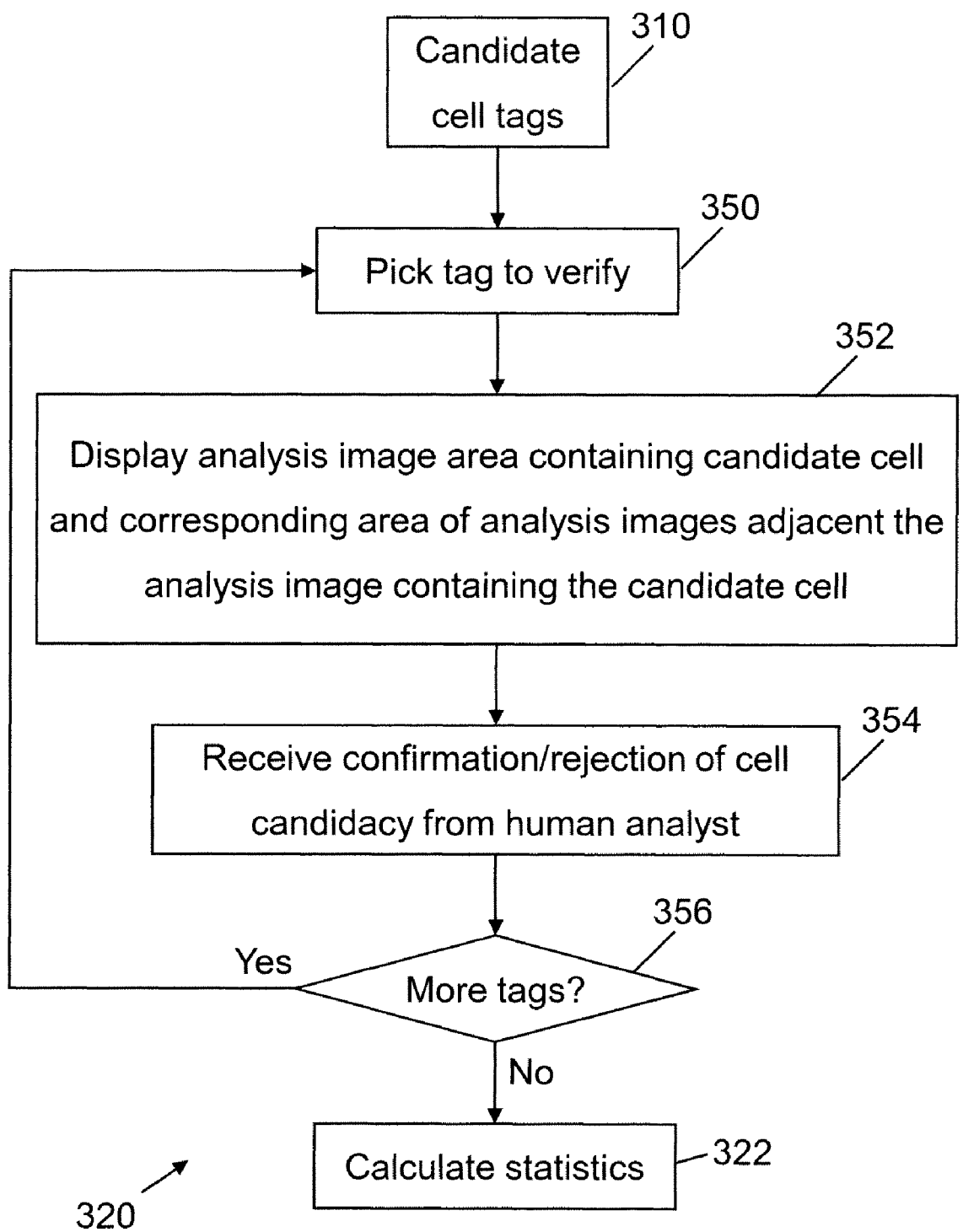
FIG. 22 diagrammatically shows a suitable user verification process for enabling a human analyst to confirm or reject candidate cells.

With reference to FIG. 22, a suitable embodiment of the optional user verification processing 320 is described. A tag is selected for verification in a selection operation 350. In a display operation 352, the area of the analysis image containing the candidate cell tag is displayed, optionally along with the corresponding area of analysis images adjacent in depth to the analysis image containing the candidate cell. Displaying the analysis images that are adjacent in depth provides the reviewing human analyst with additional views which may fortuitously include a more recognizable cell image than the analysis image in which the automated processing 306 detected the cell candidate. The human analyst either confirms or rejects the candidacy in operation 354. A loop operation 356 works though all the candidate cell tags to provide review by the human analyst of each candidate cell. The statistical analysis 322 operates on those cell candidate tags that were confirmed by the human analyst.

Example data acquisition and analysis processing has been described with reference to FIGS. 16-22 in the context of quantitative buffy coat analysis using the annular sample in the annular gap 12 between the test tube wall 14 and the float wall 16. However, it will be appreciated that the processing is readily applied to other sample scanning approaches, such as the scanning of the planar sample slide 60 depicted in FIG. 4.

The example embodiments principally relate to quantitative buffy coat analysis. However, it will be appreciated that the apparatuses and methods disclosed herein are applicable to other types of bioassays. For example, the cells can be stained rather than fluorescently tagged, or the cells may have an intrinsic optical signature (fluorescence, contrast, or so forth) that enables assessment by optical microscopy. The features assessed may be other than rare cells. For example, the assessed features may be cell fragments, bacteria, or multi-cellular structures. The sample may be a biological sample other than a buffy coat sample.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An optical system for imaging a field of view, the optical system comprising:
   an optical train configured to adjust a non-uniform distribution of source light to generate light having an adjusted non-uniform spatial distribution, the optical train including a diffuser that reduces nonuniformity of the source light and one or more focusing elements that reduce a diameter of the light output by the diffuser and couple the light output by the diffuser into an objective; and
   the objective configured to focus the light having the adjusted non-uniform spatial distribution, the focusing defining illumination light that substantially uniformly illuminates the field of view.

2. The optical system as set forth in claim 1, wherein the diffuser is tilted respective to an optical path of the optical train at a tilt angle effective to shift a speckle pattern of the source light to higher spatial frequencies whereby the frequency-shifted speckle is made substantially smaller than an imaging pixel size.

3. The optical system as set forth in claim 1, wherein the source light has a nonuniform Gaussian distribution, and the optical train generates the light having an adjusted non-uniform spatial distribution with reduced or eliminated Gaussian nonuniformity.

4. The optical system as set forth in claim 1, wherein the optical train comprises only stationary components that are not rotated, relatively oscillated, or relatively moved.

5. The optical system as set forth in claim 4, wherein the optical train and the objective are arranged to be moved as a whole respective to a sample to scan the field of view respective to the sample.

6. The optical system as set forth in claim 1, further comprising:
   a generally tubular sample holder including a test tube containing a float cooperatively defining an annular sample region coinciding with the field of view.

7. The optical system as set forth in claim 1, further comprising:
   an imaging optical sub-system including said objective, the imaging optical sub-system configured to use said objective to acquire an image of the field of view illuminated by said illumination light.

8. An imaging method comprising:
   adjusting source light having a non-uniform spatial distribution to generate light having an adjusted spatial non-uniformity;
   inputting the light having the adjusted spatial non-uniformity into an objective arranged to illuminate a field of view, focusing performed by the objective introducing further spatial non-uniformity that cancels the adjusted spatial non-uniformity such that the field of view is substantially uniformly illuminated, wherein the inputting includes reducing a diameter of the light having the adjusted spatial non-uniformity to couple the light having the adjusted spatial non-uniformity into the objective; and acquiring an image of the substantially uniformly illuminated field of view using said objective.

9. The imaging method as set forth in claim 8, wherein the source light is a substantially collimated beam of source light characterized by a first diameter, and the adjusting comprises:

expanding the substantially collimated beam of source light to produce diverging source light;

collimating the diverging source light to produce a larger-diameter substantially collimated beam of source light characterized by a second diameter that is larger than the first diameter; and processing the larger-diameter substantially collimated beam of source light to generate the light having the adjusted spatial non-uniformity.

10. The imaging method as set forth in claim 8, further comprising:

relatively scanning the field of view over an annular region of interest at least by rotating the annular region of interest respective to the objective.

11. The imaging method as set forth in claim 10, further comprising:

defining the annular region of interest by cooperation of a test tube and an insert disposed in the test tube.

12. The imaging method as set forth in claim 8, wherein the source light is diverging source light, and the adjusting comprises:

collimating the diverging source light to produce collimated source light; and processing the collimated source light to generate the light having the adjusted spatial non uniformity.

13. An optical system for imaging a field of view, the optical system comprising:

an objective focused on a field of view, wherein the objective introduces a first spatial nonuniformity to light;

an optical train generating and inputting illumination light into the objective, said illumination light cooperating with focusing performed by the objective to generate substantially uniform illumination at the field of view, wherein the illumination light input by the optical train into the objective has a second spatial nonuniformity that is canceled out by the first spatial nonuniformity introduced by the objective to generate said substantially uniform illumination at the field of view; and an imaging optical sub-system including said objective, the imaging optical sub-system configured to use the objective to acquire an image of the field of view substantially uniformly illuminated by the optical train.

14. The optical system as set forth in claim 13, further comprising:

a sample holder configured to (i) define an annular sample region coinciding with the field of view and (ii) rotate the annular sample region respective to the objective.

15. The optical system as set forth in claim 13, wherein the optical train comprises:

a diffuser configured to reduce nonuniformity of source light.

* * * * *